(12) United States Patent
Xue et al.

(10) Patent No.: US 11,807,883 B2
(45) Date of Patent: Nov. 7, 2023

(54) POLYPEPTIDE TAG, HIGHLY SOLUBLE RECOMBINANT NITRILASE AND APPLICATION THEREOF IN SYNTHESIS OF PHARMACEUTICAL CHEMICALS

(71) Applicant: ZHEJIANG UNIVERSITY OF TECHNOLOGY, Zhejiang (CN)

(72) Inventors: Yaping Xue, Zhejiang (CN); Dong Xie, Zhejiang (CN); Neng Xiong, Zhejiang (CN); Yuguo Zheng, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 0 days.

(21) Appl. No.: 17/240,715

(22) Filed: Apr. 26, 2021

(65) Prior Publication Data

US 2022/0135960 A1 May 5, 2022

(30) Foreign Application Priority Data

Nov. 3, 2020 (CN) .......................... 202011211251.6

(51) Int. Cl.
| | |
|---|---|
| *C12N 9/78* | (2006.01) |
| *C07K 7/06* | (2006.01) |
| *C12N 9/20* | (2006.01) |
| *C12P 7/42* | (2006.01) |
| *C12P 13/00* | (2006.01) |

(52) U.S. Cl.
CPC .................. *C12N 9/78* (2013.01); *C07K 7/06* (2013.01); *C12N 9/20* (2013.01); *C12P 7/42* (2013.01); *C12P 13/002* (2013.01)

(58) Field of Classification Search
None
See application file for complete search history.

(56) References Cited

U.S. PATENT DOCUMENTS

| | | | |
|---|---|---|---|
| 6,870,038 B2 * | 3/2005 | Chauhan ............... | C12P 13/002 |
| | | | 435/6.16 |
| 7,056,709 B2 * | 6/2006 | Chauhan ................. | C12P 13/02 |
| | | | 435/6.16 |
| 7,148,051 B2 * | 12/2006 | Payne ...................... | C12N 9/78 |
| | | | 536/23.1 |
| 7,198,927 B2 * | 4/2007 | DiCosimo ................. | C12P 7/42 |
| | | | 435/146 |
| 11,001,823 B2 * | 5/2021 | Xue ......................... | C12N 9/78 |

* cited by examiner

*Primary Examiner* — Hope A Robinson
(74) *Attorney, Agent, or Firm* — Muncy, Geissler, Olds & Lowe, P.C.

(57) ABSTRACT

The present invention provides a polypeptide tag and its application in the synthesis of pharmaceutical chemicals, the recombinant nitrilase was obtained by connecting a polypeptide tag to the N-terminus of the amino acid sequence of the nitrilase; wherein amino acids at both ends of the polypeptide tag are uncharged glycine G, and the rest are a random combination of any one or more of glycine G, histidine H, glutamic acid E, aspartic acid D, lysine K and arginine R; The activity of the recombinant nitrilase in the preparation of 1-cyanocyclohexyl acetic acid is up to 3034.7 U/g dcw, the polypeptide tag significantly improves the soluble expression of nitrilase, and the whole cell catalyst hydrolyzes 1M substrate with the same concentration 30 minutes faster than the mother enzyme. The method provided by the present invention can also be used for the biocatalytic reaction of other pharmaceutical intermediates as the substrate catalyzed by the nitrilase, improving the activity of the whole cell catalyst in reaction, and also improving the solubility of other types of nitrilases and the activity of the corresponding whole cell catalysts.

3 Claims, 6 Drawing Sheets

Specification includes a Sequence Listing.

SEQUENCE LISTING

<160> NUMBER OF SEQ ID NOS: 99

<210> SEQ ID NO 1
<211> LENGTH: 369
<212> TYPE: PRT
<213> ORGANISM: Acidovorax facilis

<400> SEQUENCE: 1

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Phe Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285
```

Ala Gly Ala Asp Pro Val Gly His Tyr Ser Arg Pro Asp Val Leu Ser
            290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Lys Ala Ala Glu Lys Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 2
<211> LENGTH: 1110
<212> TYPE: DNA
<213> ORGANISM: Acidovorax facilis

<400> SEQUENCE: 2
atggtatctt acaactccaa atttctggct gctaccgtac aggctgaacc ggtttggctg      60
gacgcggacg caactatcga taatctatt ggtatcatcg aggaggcggc ccagaaaggt     120
gcgtctctga ttgccttccc ggaagttttc atccctggtt acccgtattg ggcctggctg     180
ggtgacgtaa agtactccct gtccttcacc tcccgttacc acgaaaactc cctggaactg     240
ggtgacgacc gtatgcgccg tctgcaactg gctgcgcgtc gtaacaaaat cgcgctggtt     300
atgggttaca gcgagcgtga ggcaggcagc cgctacctgt cccaggtctt tatcgacgaa     360
cgtggtgaaa tcgttgctaa ccgtcgtaaa ctgaaaccaa ctcacgttga acgtacgatt     420
tatggtgaag caacggtac cgactttctg acgcatgact cgcatttgg tcgtgttggt      480
ggtctgaact gctgggagca ctttcagccg ctgtccaaat tcatgatgta ctccctgggt     540
gaacaggtac acgtcgcttc ttggccggct atgtccccgc tgcaaccgga cgtgtttcaa     600
ttttccatcg aggctaatgc gaccgtaacc cgctcctatg ctattgaagg ccaaaccttc     660
gttctgtgct ctacgcaggt tatcggtccg tctgcaattg aaaccttctg tctgaacgat     720
gagcaacgtg cactgctgcc gcagggttgc ggttgggcgc gtatctacgg cccggacggc     780
agcgaactgg ccaagccgct ggctgaagac gcagagggta ttctgtacgc agaaatcgat     840
ctggaacaga ttctgctggc caaggctggc gctgatccgg ttggtcacta cagccgccct     900
gatgtcctgt ccgtgcagtt cgacccgcgt aaccacaccc cggtacaccg cattggtatc     960
gatggccgtc tggatgttaa cacgcgttcc cgtgtagaaa actttcgcct gcgtaaagca    1020
gcagaaaaag aacgtcaggc cagcaaacgt ctgggcacga aactgtttga acagtctctg    1080
ctggcggagg agccggtacc agccaaatag                                     1110

<210> SEQ ID NO 3
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 3

Gly Lys Gly Lys Gly
1               5

<210> SEQ ID NO 4

```
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 4

Gly Lys Gly Glu Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 5

Gly Lys Gly His Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 6

Gly Arg Gly Arg Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 7

Gly Arg Gly Gly Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 8

Gly His Gly His Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 9

Gly Asp Gly Asp Gly
1               5

<210> SEQ ID NO 10
<211> LENGTH: 5
```

```
<212> TYPE: PRT
<213> ORGANISM: Artificial Sequence
<220> FEATURE:
<223> OTHER INFORMATION: Synthetic: polypeptide tag

<400> SEQUENCE: 10

Gly Asp Gly Glu Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 11

Gly Asp Gly Arg Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 12

Gly Asp Gly Lys Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 13

Gly Glu Gly Glu Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 14

Gly Glu Gly Lys Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 15

Gly Glu Gly Gly Gly
1               5

<210> SEQ ID NO 16
<211> LENGTH: 5
<212> TYPE: PRT
```

```
<213> ORGANISM: Artificial Sequence
<220> FEATURE:
<223> OTHER INFORMATION: Synthetic: polypeptide tag

<400> SEQUENCE: 16

Gly Glu Gly Arg Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 17

Gly Glu Gly Asp Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 18

Gly Lys Gly Asp Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 19

Gly Lys Gly Gly Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 20

Gly Lys Gly Arg Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 21

Gly Arg Gly Asp Gly
1               5

<210> SEQ ID NO 22
<211> LENGTH: 5
<212> TYPE: PRT
<213> ORGANISM: Artificial Sequence
```

```
<220> FEATURE:
<223> OTHER INFORMATION: Synthetic: polypeptide tag

<400> SEQUENCE: 22

Gly Arg Gly Glu Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 23

Gly Arg Gly Lys Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 24

Gly Gly Gly Lys Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 25

Gly Gly Gly Glu Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic: polypeptide tag

<400> SEQUENCE: 26

Gly Lys Gly Lys Gly Lys Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic: polypeptide tag

<400> SEQUENCE: 27

Gly Lys Gly Lys Gly Lys Gly Lys Gly
1               5

<210> SEQ ID NO 28
<211> LENGTH: 11
<212> TYPE: PRT
<213> ORGANISM: Artificial Sequence
<220> FEATURE:
```

```
<223> OTHER INFORMATION: Synthetic: polypeptide tag

<400> SEQUENCE: 28

Gly Lys Gly Lys Gly Lys Gly Lys Gly Lys Gly
1               5                   10

<210> SEQ ID NO 29
<211> LENGTH: 4
<212> TYPE: PRT
<213> ORGANISM: Artificial Sequence
<220> FEATURE:
<223> OTHER INFORMATION: Synthetic: polypeptide tag

<400> SEQUENCE: 29

Gly Gly Gly Ser
1

<210> SEQ ID NO 30
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 30

Gly Gly Gly Gly Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic: polypeptide tag

<400> SEQUENCE: 31

Gly Lys Gly Lys Gly Gly Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic: polypeptide tag

<400> SEQUENCE: 32

Gly Lys Gly Lys Gly Gly Gly Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic: polypeptide tag

<400> SEQUENCE: 33

Gly Lys Gly Lys Gly Gly Gly Gly Ser
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic: polypeptide tag
```

<400> SEQUENCE: 34

Gly Lys Gly Lys Gly Gly Gly Gly Ser
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Synthetic: polypeptide tag

<400> SEQUENCE: 35

Gly Asp Gly Gly Gly
1               5

<210> SEQ ID NO 36
<211> LENGTH: 20
<212> TYPE: DNA
<213> ORGANISM: Artificial Sequence
<220> FEATURE:
<223> OTHER INFORMATION: Synthetic primer: T7

<400> SEQUENCE: 36
taatacgact cactataggg                                          20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer: T7 ter

<400> SEQUENCE: 37
tgctagttat tgctcagcgg                                          20

<210> SEQ ID NO 38
<211> LENGTH: 36
<212> TYPE: DNA
<213> ORGANISM: Artificial Sequence
<220> FEATURE:
<223> OTHER INFORMATION: Synthetic primer: GDGDG-F

<400> SEQUENCE: 38
accatgggtg atggtgatgg tgtatcttac aactcc                        36

<210> SEQ ID NO 39
<211> LENGTH: 38
<212> TYPE: DNA
<213> ORGANISM: Artificial Sequence
<220> FEATURE:
<223> OTHER INFORMATION: Synthetic primer: GDGDG-R

<400> SEQUENCE: 39
gtaagataca ccatcaccat cacccatggt atatctcc                      38

<210> SEQ ID NO 40
<211> LENGTH: 36
<212> TYPE: DNA
<213> ORGANISM: Artificial Sequence
<220> FEATURE:
<223> OTHER INFORMATION: Synthetic primer: GDGEG-F

<400> SEQUENCE: 40
accatgggtg atggtgaagg tgtatcttac aactcc                        36

<210> SEQ ID NO 41
<211> LENGTH: 38
<212> TYPE: DNA
<213> ORGANISM: Artificial Sequence
<220> FEATURE:
<223> OTHER INFORMATION: Synthetic primer: GDGEG-R

<400> SEQUENCE: 41
gtaagataca ccttcaccat cacccatggt atatctcc                               38

<210> SEQ ID NO 42
<211> LENGTH: 37
<212> TYPE: DNA
<213> ORGANISM: Artificial Sequence
<220> FEATURE:
<223> OTHER INFORMATION: Synthetic primer: GDGRG-F

<400> SEQUENCE: 42
taccatgggt gatggtcgag gtgtatctta caactcc                                37

<210> SEQ ID NO 43
<211> LENGTH: 38
<212> TYPE: DNA
<213> ORGANISM: Artificial Sequence
<220> FEATURE:
<223> OTHER INFORMATION: Synthetic primer: GDGRG-R

<400> SEQUENCE: 43
gatacacctc gaccatcacc catggtatat ctccttct                               38

<210> SEQ ID NO 44
<211> LENGTH: 29
<212> TYPE: DNA
<213> ORGANISM: Artificial Sequence
<220> FEATURE:
<223> OTHER INFORMATION: Synthetic primer: GDGKG-F

<400> SEQUENCE: 44
taccatgggt gatggtaaag gtgtatctt                                         29

<210> SEQ ID NO 45
<211> LENGTH: 31
<212> TYPE: DNA
<213> ORGANISM: Artificial Sequence
<220> FEATURE:
<223> OTHER INFORMATION: Synthetic primer: GDGKG-R

<400> SEQUENCE: 45
gaaatttgga gttgtaagat acaccatcac c                                      31

<210> SEQ ID NO 46
<211> LENGTH: 29
<212> TYPE: DNA
<213> ORGANISM: Artificial Sequence
<220> FEATURE:
<223> OTHER INFORMATION: Synthetic primer: GDGGG-F

<400> SEQUENCE: 46
taccatgggt gatggtggtg gtgtatctt                                         29

<210> SEQ ID NO 47
<211> LENGTH: 31
<212> TYPE: DNA
<213> ORGANISM: Artificial Sequence
<220> FEATURE:
<223> OTHER INFORMATION: Synthetic primer: GDGGG-R

<400> SEQUENCE: 47
gaaatttgga gttgtaagat acaccaccac c                                31

<210> SEQ ID NO 48
<211> LENGTH: 25
<212> TYPE: DNA
<213> ORGANISM: GEGEG-F

<400> SEQUENCE: 48
catgggtgaa ggtgaaggtg tatct                                       25

<210> SEQ ID NO 49
<211> LENGTH: 24
<212> TYPE: DNA
<213> ORGANISM: Artificial Sequence
<220> FEATURE:
<223> OTHER INFORMATION: Synthetic primer: GEGGE-R

<400> SEQUENCE: 49
accttcacct tcacccatgg tata                                        24

<210> SEQ ID NO 50
<211> LENGTH: 25
<212> TYPE: DNA
<213> ORGANISM: Artificial Sequence
<220> FEATURE:
<223> OTHER INFORMATION: Synthetic primer: GEGKG-F

<400> SEQUENCE: 50
catgggtgaa ggtgaaggtg tatct                                       25

<210> SEQ ID NO 51
<211> LENGTH: 24
<212> TYPE: DNA
<213> ORGANISM: Artificial Sequence
<220> FEATURE:
<223> OTHER INFORMATION: Synthetic primer: GEGKG-R

<400> SEQUENCE: 51
accttcacct tcacccatgg tata                                        24

<210> SEQ ID NO 52
<211> LENGTH: 28
<212> TYPE: DNA
<213> ORGANISM: Artificial Sequence
<220> FEATURE:
<223> OTHER INFORMATION: Synthetic primer: GEGGG-F

<400> SEQUENCE: 52
taccatgggt gaaggtggtg gtgtatct                                    28

<210> SEQ ID NO 53
<211> LENGTH: 32
<212> TYPE: DNA
<213> ORGANISM: Artificial Sequence
<220> FEATURE:
<223> OTHER INFORMATION: Synthetic primer: GEGGG-R

<400> SEQUENCE: 53
agttgtaaga tacaccacca ccttcaccca tg                               32

<210> SEQ ID NO 54
<211> LENGTH: 28
<212> TYPE: DNA

<210> SEQ ID NO 55
<211> LENGTH: 32
<212> TYPE: DNA
<213> ORGANISM: Artificial Sequence
<220> FEATURE:
<223> OTHER INFORMATION: Synthetic primer: GEGRG-F

<400> SEQUENCE: 54
taccatgggt gaaggtcgag gtgtatct          28

<210> SEQ ID NO 55
<211> LENGTH: 32
<212> TYPE: DNA
<213> ORGANISM: Artificial Sequence
<220> FEATURE:
<223> OTHER INFORMATION: Synthetic primer: GEGRG-R

<400> SEQUENCE: 55
agttgtaaga tacacctcga ccttcaccca tg          32

<210> SEQ ID NO 56
<211> LENGTH: 25
<212> TYPE: DNA
<213> ORGANISM: Artificial Sequence
<220> FEATURE:
<223> OTHER INFORMATION: Synthetic primer: GEGDG-F

<400> SEQUENCE: 56
catgggtgaa ggtgatggtg tatct          25

<210> SEQ ID NO 57
<211> LENGTH: 24
<212> TYPE: DNA
<213> ORGANISM: Artificial Sequence
<220> FEATURE:
<223> OTHER INFORMATION: Synthetic primer: GEGDG-R

<400> SEQUENCE: 57
accatcacct tcacccatgg tata          24

<210> SEQ ID NO 58
<211> LENGTH: 28
<212> TYPE: DNA
<213> ORGANISM: Artificial Sequence
<220> FEATURE:
<223> OTHER INFORMATION: Synthetic primer: GKGKG-F

<400> SEQUENCE: 58
ggtaaaggta aggtgtatc ttacaact          28

<210> SEQ ID NO 59
<211> LENGTH: 23
<212> TYPE: DNA
<213> ORGANISM: Artificial Sequence
<220> FEATURE:
<223> OTHER INFORMATION: Synthetic primer: GKGKG-R

<400> SEQUENCE: 59
tacaccttta cctttaccca tgg          23

<210> SEQ ID NO 60
<211> LENGTH: 36
<212> TYPE: DNA
<213> ORGANISM: Artificial Sequence
<220> FEATURE:
<223> OTHER INFORMATION: Synthetic primer: GKGDG-F

<400> SEQUENCE: 60
accatgggta aggtgatgg tgtatcttac aactcc          36

<210> SEQ ID NO 61
<211> LENGTH: 38
<212> TYPE: DNA
<213> ORGANISM: Artificial Sequence
<220> FEATURE:
<223> OTHER INFORMATION: Synthetic primer: GKGDG-R

<400> SEQUENCE: 61
gtaagataca ccatcacctt tacccatggt atatctcc         38

<210> SEQ ID NO 62
<211> LENGTH: 36
<212> TYPE: DNA
<213> ORGANISM: Artificial Sequence
<220> FEATURE:
<223> OTHER INFORMATION: Synthetic primer: GKGEG-F

<400> SEQUENCE: 62
accatgggta aggtgaagg tgtatcttac aactcc           36

<210> SEQ ID NO 63
<211> LENGTH: 38
<212> TYPE: DNA
<213> ORGANISM: Artificial Sequence
<220> FEATURE:
<223> OTHER INFORMATION: Synthetic primer: GKGEG-R

<400> SEQUENCE: 63
gtaagataca ccttcacctt tacccatggt atatctcc         38

<210> SEQ ID NO 64
<211> LENGTH: 34
<212> TYPE: DNA
<213> ORGANISM: Artificial Sequence
<220> FEATURE:
<223> OTHER INFORMATION: Synthetic primer: GKGGG-F

<400> SEQUENCE: 64
taccatgggt aaaggtgttg gtgtatctta caac            34

<210> SEQ ID NO 65
<211> LENGTH: 34
<212> TYPE: DNA
<213> ORGANISM: Artificial Sequence
<220> FEATURE:
<223> OTHER INFORMATION: Synthetic primer: GKGGG-R

<400> SEQUENCE: 65
tacaccaaca cctttaccca tggtatatct cctt            34

<210> SEQ ID NO 66
<211> LENGTH: 38
<212> TYPE: DNA
<213> ORGANISM: Artificial Sequence
<220> FEATURE:
<223> OTHER INFORMATION: Synthetic primer: GKGHG-F

<400> SEQUENCE: 66
taccatgggt aaaggtcacg gtgtatctta caactcca         38

<210> SEQ ID NO 67
<211> LENGTH: 36
<212> TYPE: DNA
<213> ORGANISM: Artificial Sequence
<220> FEATURE:

<223> OTHER INFORMATION: Synthetic primer: GKGHG-R

<400> SEQUENCE: 67 gataccaccgt gacctttacc catggtatat ctcctt    36

<210> SEQ ID NO 68
<211> LENGTH: 38
<212> TYPE: DNA
<213> ORGANISM: Artificial Sequence
<220> FEATURE:
<223> OTHER INFORMATION: Synthetic primer: GKGRG-F

<400> SEQUENCE: 68
taccatgggt aaaggtcgag gtgtatctta caactcca    38

<210> SEQ ID NO 69
<211> LENGTH: 36
<212> TYPE: DNA
<213> ORGANISM: Artificial Sequence
<220> FEATURE:
<223> OTHER INFORMATION: Synthetic primer: GKGRG-R

<400> SEQUENCE: 69
gatacacctc gacctttacc catggtatat ctcctt    36

<210> SEQ ID NO 70
<211> LENGTH: 37
<212> TYPE: DNA
<213> ORGANISM: Artificial Sequence
<220> FEATURE:
<223> OTHER INFORMATION: Synthetic primer: GRGRG-F

<400> SEQUENCE: 70
taccatgggt cgaggtcgag gtgtatctta caactcc    37

<210> SEQ ID NO 71
<211> LENGTH: 38
<212> TYPE: DNA
<213> ORGANISM: Artificial Sequence
<220> FEATURE:
<223> OTHER INFORMATION: Synthetic primer: GRGRG-R

<400> SEQUENCE: 71
gatacacctc gacctcgacc catggtatat ctccttct    38

<210> SEQ ID NO 72
<211> LENGTH: 33
<212> TYPE: DNA
<213> ORGANISM: Artificial Sequence
<220> FEATURE:
<223> OTHER INFORMATION: Synthetic primer: GRGDG-F

<400> SEQUENCE: 72
accatgggtc gtggtgatgg tgtatcttac aac    33

<210> SEQ ID NO 73
<211> LENGTH: 32
<212> TYPE: DNA
<213> ORGANISM: Artificial Sequence
<220> FEATURE:
<223> OTHER INFORMATION: Synthetic primer: GRGDG-R

<400> SEQUENCE: 73 ataccaccatc accacgaccc atggtaatct cc    32

<210> SEQ ID NO 74
<211> LENGTH: 33
<212> TYPE: DNA
<213> ORGANISM: Artificial Sequence
<220> FEATURE:
<223> OTHER INFORMATION: Synthetic primer: GRGEG-F

<400> SEQUENCE: 74
accatgggtc gtggtgaagg tgtatcttac aac                33

<210> SEQ ID NO 75
<211> LENGTH: 32
<212> TYPE: DNA
<213> ORGANISM: Artificial Sequence
<220> FEATURE:
<223> OTHER INFORMATION: Synthetic primer: GRGEG-R

<400> SEQUENCE: 75
atacaccttc accacgaccc atggtaatct cc                 32

<210> SEQ ID NO 76
<211> LENGTH: 38
<212> TYPE: DNA
<213> ORGANISM: Artificial Sequence
<220> FEATURE:
<223> OTHER INFORMATION: Synthetic primer: GRGKG-F

<400> SEQUENCE: 76
taccatgggt cgaggtaaag gtgtatctta caactcca           38

<210> SEQ ID NO 77
<211> LENGTH: 36
<212> TYPE: DNA
<213> ORGANISM: Artificial Sequence
<220> FEATURE:
<223> OTHER INFORMATION: Synthetic primer: GRGKG-R

<400> SEQUENCE: 77 gataccctt tacctcgacc catggtatat ctcctt              36

<210> SEQ ID NO 78
<211> LENGTH: 33
<212> TYPE: DNA
<213> ORGANISM: Artificial Sequence
<220> FEATURE:
<223> OTHER INFORMATION: Synthetic primer: GRGGG-F

<400> SEQUENCE: 78
accatgggtc gtggtggtgg tgtatcttac aac                33

<210> SEQ ID NO 79
<211> LENGTH: 32
<212> TYPE: DNA
<213> ORGANISM: Artificial Sequence
<220> FEATURE:
<223> OTHER INFORMATION: Synthetic primer: GRGGG-R

<400> SEQUENCE: 79
atacaccacc accacgaccc atggtaatct cc                 32

<210> SEQ ID NO 80
<211> LENGTH: 29
<212> TYPE: DNA
<213> ORGANISM: Artificial Sequence
<220> FEATURE:
<223> OTHER INFORMATION: Synthetic primer: GGGKG-F

```
<400> SEQUENCE: 80
taccatgggt ggtggtaaag gtgtatctt                              29

<210> SEQ ID NO 81
<211> LENGTH: 31
<212> TYPE: DNA
<213> ORGANISM: Artificial Sequence
<220> FEATURE:
<223> OTHER INFORMATION: Synthetic primer: GGGKG-R

<400> SEQUENCE: 81
gaaatttgga gttgtaagat acacctttac c                           31

<210> SEQ ID NO 82
<211> LENGTH: 26
<212> TYPE: DNA
<213> ORGANISM: Artificial Sequence
<220> FEATURE:
<223> OTHER INFORMATION: Synthetic primer: GGGEG-F

<400> SEQUENCE: 82
taccatgggt ggtggtgaag gtgtat                                 26

<210> SEQ ID NO 83
<211> LENGTH: 29
<212> TYPE: DNA
<213> ORGANISM: Artificial Sequence
<220> FEATURE:
<223> OTHER INFORMATION: Synthetic primer: GGGEG-R

<400> SEQUENCE: 83
ttgtaagata caccttcacc accacccat                              29

<210> SEQ ID NO 84
<211> LENGTH: 38
<212> TYPE: DNA
<213> ORGANISM: Artificial Sequence
<220> FEATURE:
<223> OTHER INFORMATION: Synthetic primer: GHGHG-F

<400> SEQUENCE: 84
taccatgggt cacggtcacg gtgtatctta caactcca                    38

<210> SEQ ID NO 85
<211> LENGTH: 36
<212> TYPE: DNA
<213> ORGANISM: Artificial Sequence
<220> FEATURE:
<223> OTHER INFORMATION: Synthetic primer: GHGHG-R

<400> SEQUENCE: 85
gatacaccgt gaccgtgacc catggtatat ctcctt                      36

<210> SEQ ID NO 86
<211> LENGTH: 37
<212> TYPE: DNA
<213> ORGANISM: Artificial Sequence
<220> FEATURE:
<223> OTHER INFORMATION: Synthetic primer: GKGKGKG-F

<400> SEQUENCE: 86
accatgggta aaggtaaagg taaaggtgta tcttaca                     37

<210> SEQ ID NO 87
<211> LENGTH: 35
```

```
<212> TYPE: DNA
<213> ORGANISM: Artificial Sequence
<220> FEATURE:
<223> OTHER INFORMATION: Synthetic primer: GKGKGKG-R

<400> SEQUENCE: 87
tggagttgta agatacacct ttacctttac cttta                           35

<210> SEQ ID NO 88
<211> LENGTH: 42
<212> TYPE: DNA
<213> ORGANISM: Artificial Sequence
<220> FEATURE:
<223> OTHER INFORMATION: Synthetic primer: GKGKGKGKG-F

<400> SEQUENCE: 88
accatgggta aggtaaagg taaaggtaaa ggtgtatctt ac                    42

<210> SEQ ID NO 89
<211> LENGTH: 41
<212> TYPE: DNA
<213> ORGANISM: Artificial Sequence
<220> FEATURE:
<223> OTHER INFORMATION: Synthetic primer: GKGKGKGKG-R

<400> SEQUENCE: 89
tggagttgta agatacacct ttacctttac ctttaccttt a                    41

<210> SEQ ID NO 90
<211> LENGTH: 48
<212> TYPE: DNA
<213> ORGANISM: Artificial Sequence
<220> FEATURE:
<223> OTHER INFORMATION: Synthetic primer: GKGKGKGKGKG-F

<400> SEQUENCE: 90
accatgggta aggtaaagg taaaggtaaa ggtaaaggtg tatcttac              48

<210> SEQ ID NO 91
<211> LENGTH: 66
<212> TYPE: DNA
<213> ORGANISM: Artificial Sequence
<220> FEATURE:
<223> OTHER INFORMATION: Synthetic primer: GKGKGKGKGKG-R

<400> SEQUENCE: 91
taaaggtaaa ggtggttctg tatcttacaa ctccaagata cagaaccacc tttaccttta  60
cccatg                                                           66

<210> SEQ ID NO 92
<211> LENGTH: 41
<212> TYPE: DNA
<213> ORGANISM: Artificial Sequence
<220> FEATURE:
<223> OTHER INFORMATION: Synthetic primer: GKGKG-GS-F

<400> SEQUENCE: 92
taaaggtaaa ggtggttctg gttctgtatc ttacaactcc a                    41

<210> SEQ ID NO 93
<211> LENGTH: 37
<212> TYPE: DNA
<213> ORGANISM: Artificial Sequence
<220> FEATURE:
<223> OTHER INFORMATION: Synthetic primer: GKGKG-GS-R
```

<210> SEQ ID NO 93
<211> LENGTH: 37
<212> TYPE: DNA
<213> ORGANISM: Artificial Sequence
<220> FEATURE:
<223> OTHER INFORMATION: Synthetic primer: GKGKG-GGS-F

<400> SEQUENCE: 93
agatacagaa ccagaaccac ctttaccttt acccatg        37

<210> SEQ ID NO 94
<211> LENGTH: 38
<212> TYPE: DNA
<213> ORGANISM: Artificial Sequence
<220> FEATURE:
<223> OTHER INFORMATION: Synthetic primer: GKGKG-GGS-F

<400> SEQUENCE: 94
taaaggtaaa ggtggtggtt ctgtatctta caactcca        38

<210> SEQ ID NO 95
<211> LENGTH: 34
<212> TYPE: DNA
<213> ORGANISM: Artificial Sequence
<220> FEATURE:
<223> OTHER INFORMATION: Synthetic primer: GKGKG-GGS-R

<400> SEQUENCE: 95
agatacagaa ccaccacctt tacctttacc catg        34

<210> SEQ ID NO 96
<211> LENGTH: 41
<212> TYPE: DNA
<213> ORGANISM: Artificial Sequence
<220> FEATURE:
<223> OTHER INFORMATION: Synthetic primer: GKGKG-GGGS-F

<400> SEQUENCE: 96
taaaggtaaa ggtggtggtg gttctgtatc ttacaactcc a        41

<210> SEQ ID NO 97
<211> LENGTH: 37
<212> TYPE: DNA
<213> ORGANISM: Artificial Sequence
<220> FEATURE:
<223> OTHER INFORMATION: Synthetic primer: GKGKG-GGGS-R

<400> SEQUENCE: 97
agatacagaa ccaccaccac ctttaccttt acccatg        37

<210> SEQ ID NO 98
<211> LENGTH: 42
<212> TYPE: DNA
<213> ORGANISM: Artificial Sequence
<220> FEATURE:
<223> OTHER INFORMATION: Synthetic primer: GKGKG-GGGGS-F

<400> SEQUENCE: 98
taaaggtaaa ggtggtggtg gtggttctgt atcttacaac tc        42

<210> SEQ ID NO 99
<211> LENGTH: 40
<212> TYPE: DNA
<213> ORGANISM: Artificial Sequence
<220> FEATURE:
<223> OTHER INFORMATION: Synthetic primer: GKGKG-GGGGS-R

<400> SEQUENCE: 99
agatacagaa ccaccaccac cacctttacc tttacccatg        40

POLYPEPTIDE TAG, HIGHLY SOLUBLE RECOMBINANT NITRILASE AND APPLICATION THEREOF IN SYNTHESIS OF PHARMACEUTICAL CHEMICALS

The instant application contains a Sequence Listing which has been submitted electronically in the ASCII text file and is hereby incorporated by reference in its entirety. The ASCII text file is a sequence listing entitled "2022-08-18-Seq-Listing" created on Aug. 18, 2022 and having a size of 23,648 bytes in compliance of 37 CFR 1.821.

CROSS REFERENCE TO RELATED APPLICATIONS

This application claims priority of Application No. 202011211251.6 filed in China on Nov. 3, 2020 under 35 U.S.C. § 119, the entire contents of which are hereby incorporated by reference.

TECHNICAL FIELD

The present invention relates to a polypeptide tag, in particular to a universal polypeptide tag that can enhance soluble expression of enzymes such as nitrilase and application thereof in synthesis of pharmaceutical chemicals, belonging to the technical fields of genetic engineering and protein engineering.

BACKGROUND ART

Nitrilases (EC 3.5.5.1) are an important type of hydrolases with a Glu-Lys-Cys catalytical triad, which can selectively and effectively catalyze the hydrolysis of cyano groups to carboxyl groups in a one-step reaction. And they are widely used in the synthesis of chemical products such as organic acids, amino acids and vitamins and pharmaceutical chemicals such as gabapentin, clopidogrel, baclofen, atorvastatin.

So far, many effective methods to improve soluble expression level of a protein have been reported, one is construction of a recombinant periplasmic-leaky strain or co-expression of the protein with a periplasmic chaperone protein, and another method is addition of a fusion tag (also called fusion partner or solubility tag) for collaborative expression. But these methods more or less have some drawbacks. For example, selection of amino acids of a polypeptide tag and the length of the sequence may have great side effects on the enzyme activity, stability, solubility or selectivity of the recombinant enzyme, and some tags may even change the structure of a protein enzyme which causes the enzyme to lose its activity completely. Regarding the structure of different enzymes and the charged properties of the whole protein in the catalytic system, the introduction of different polypeptide tags will bring different effects. Therefore, it is necessary to combine technologies such as kinetic simulation and homology modeling to assist in tag design. However, one of the advantages of an effective polypeptide tag is that the protein enzyme connected to it can function without removing it. Wherein, Sun-Ki Kim developed a novel polyanionic polypeptide tag, which significantly improved the expression level of Candida antarctica lipase and the efficiency of extracellular transport. In addition, Han et al. developed a novel fusion tag [HE-MBP(Pyr)] to improve the solubility of recombinant proteins4 in E. coli., and the studies showed that the solubility of the target proteins (such as monoclonal antibodies, antigen proteins and polymer proteins) was improved to varying degrees.

In biosynthetic methods, processes involving biocatalysis are usually carried out using whole cell catalysts (wet cells). It is generally believed that the volumetric enzyme activity of the fermentation broth in enzyme-producing fermentation is a combination of specific enzyme activity and soluble expression level. Increasing the specific enzyme activity or the quantity of functional proteins without affecting the original characteristics will further promote catalytic performance of the whole cells. Therefore, increasing solubility of nitrilase in E. coli is of great significance. However, increasing the solubility of the enzyme produced by E. coli always comes at the expense of activity. Therefore, a reasonable increase in the solubility of nitrilase without lowering the catalytic level to realize efficient production of 1-cyanocyclohexyl acetic acid (1-CA), an intermediate of gabapentin, still needs further research.

SUMMARY OF THE INVENTION

The object of the present invention is to provide a polypeptide tag, a recombinant enzyme containing the said polypeptide tag and its application in the synthesis of pharmaceutical chemicals. The polypeptide tag can effectively promote the whole cell catalyst activity and thermal stability of the host recombinant enzyme, and solve the problems such as poor thermal stability and insufficient enzyme activity for large-scale industrial applications.

The present invention adopts the technical solution as follows:

The present invention provides a polypeptide tag, wherein the length of the said polypeptide tag is 5-11 amino acids, amino acids at both ends of the said polypeptide tag are uncharged glycine (G), and the rest are a random combination of any one or more of glycine (G), histidine (H), glutamic acid (E), aspartic acid (D), lysine (K) and arginine (R).

Further, the amino acid sequence of the said polypeptide tag is one of the following: GKGKG(SEQ ID NO: 3), GKGEG(SEQ ID NO: 4), GKGHG(SEQ ID NO: 5), GRGRG(SEQ ID NO: 6), GRGGG(SEQ ID NO: 7), GHGHG(SEQ ID NO: 8), GDGDG(SEQ ID NO: 9), GDGEG(SEQ ID NO: 10), GDGRG(SEQ ID NO: 11), GDGKG(SEQ ID NO: 12), GEGEG(SEQ ID NO: 13), GEGKG(SEQ ID NO: 14), GEGGG(SEQ ID NO: 15), GEGRG(SEQ ID NO: 16), GEGDG(SEQ ID NO: 17), GKGDG(SEQ ID NO: 18), GKGGG(SEQ ID NO: 19), GKGRG(SEQ ID NO: 20), GRGDG(SEQ ID NO: 21), GRGEG(SEQ ID NO: 22), GRGKG(SEQ ID NO: 23), GGGKG(SEQ ID NO: 24), GGGEG(SEQ ID NO: 25), GKGKGKG(SEQ ID NO: 26), GKGKGKGKG(SEQ ID NO: 27), or GKGKGKGKGKG(SEQ ID NO: 28).

Further, it is preferred that amino acids at both ends and the middle position of the polypeptide tag are all uncharged glycine (G), and the rest are a random combination of any one or more of glycine (G), histidine (H), glutamic acid (E), aspartic acid (D), lysine (K) and arginine (R), more preferably the amino acids constitute an amino acid sequence with palindrome elements.

Further, the polypeptide tag has a linker peptide, and the amino acid sequence of the linker peptide is one of the following: GS, GGS, GGGS(SEQ ID NO: 29), GGGGS (SEQ ID NO: 30).

Furthermore, the polypeptide tag is preferably GKGKG (SEQ ID NO: 3).

The present invention provides recombinant enzymes containing the polypeptide tag and the enzymes include nitrilase, lipase, or deacylase.

Further, the recombinant enzyme is preferably a recombinant nitrilase, which is obtained by connecting the polypeptide tag to the N-terminus of the amino acid sequence of the nitrilase. The connection can be carried out by PCR amplification, one-step cloning, etc., for example, using a vector containing the nitrilase gene (preferably pET-28b(+)/AcN-M) as a template, primers containing the polypeptide tag are designed, and the PCR amplification is carried out to obtain the nitrilase containing the polypeptide tag.

Further, polypeptide tag uses one of the following connection to connect to the nitrilase by a linker peptide: GKGKG-GS(SEQ ID NO: 31), GKGKG-GGS(SEQ ID NO: 32), GKGKG-GGGS(SEQ ID NO: 33), or GKGKG-GGGGS(SEQ ID NO: 34).

The nitrilase gene of the present invention is cloned from *Acidovorax facilis* ZJB09122, and the amino acid sequence is shown in SEQ ID NO:1, and the nucleotide sequence is shown in SEQ ID NO:2.

The present invention also relates to a recombinant plasmid containing the encoding gene of the recombinant enzyme containing the polypeptide tag (preferably a recombinant plasmid of the encoding gene of the recombinant nitrilase), and the recombinant plasmid is constructed with pET-28b(+) as a vector, specifically as follows: using a plasmid containing the gene of the recombinant enzyme as a template, primers containing a polypeptide tag are designed, and whole plasmid PCR, nucleic acid gel electrophoresis and sequencing for verification are carried out to finally obtain the recombinant plasmid.

The present invention also provides a genetically engineered recombinant strain constructed from the encoding gene of the recombinant enzyme containing the polypeptide tag, and the genetically engineered recombinant strain is constructed by transferring the vector pET-28b(+) containing the encoding gene of the polypeptide tag into a host strain; and the host strain is preferably *Escherichia coli* BL21 (DE3).

The present invention also provides an application of the recombinant enzyme containing the polypeptide tag in producing a gabapentin intermediate 1-cyanocyclohexyl acetic acid, wherein the application is carried out as follows: a conversion system is built using wet cells or pure enzyme purified from the wet cells as a catalyst (preferably recombinant nitrilase), 1-cyanocyclohexylacetonitrile (1-CN) as a substrate, and a pH=7.0, 0.2 M $Na_2HPO_4$—$NaH_2PO_4$ buffer as a reaction medium, wherein the wet cells are obtained from fermentation cultivation of a genetically engineered recombinant strain that contains the encoding gene of the recombinant enzyme comprising the polypeptide tag, and in the conversion system; the reaction is carried out in a constant temperature water bath at 35° C. and 200 rpm to obtain a conversion solution containing 1-cyanocyclohexyl acetic acid, and the conversion solution is subjected to isolation and purification to obtain 1-cyanocyclohexyl acetic acid; 1-cyanocyclohexyl acetic acid is subjected to steps such as subsequent hydrogenation to obtain gabapentin; and in the conversion system, the final concentration of the substrate is 1-2M and the amount of the catalyst calculated by the weight of the wet cells is 50 g/L.

Further, the wet cells are prepared as follows: the genetically engineered recombinant strain containing the encoding gene of the recombinant enzyme containing the polypeptide tag (the recombinant nitrilase) is inoculated into LB (Luria-Bertani) medium and cultivated at 37° C. for 12-14 hours to obtain single colonies; the single colonies are picked, inoculated to LB medium containing 0.5 μg/mL kanamycin, and cultivated at 37° C. for 8 h, the resulting inoculum is inoculated to a fermentation medium containing 0.5 μg/mL kanamycin with 2% incubating volume and cultivated at 37° C. for 2 h, and then IPTG is added with the final concentration of 0.1 mM, and the bacteria solution is induced to produce the enzyme at 28° C. for 12-14 h and subjected to centrifugation at 12,000 rpm for 10 min, the resulting precipitate is washed with 0.9% saline twice, and the collected wet cells is the catalyst. The fermentation medium consists of 20 g/L yeast powder, 15 g/L sucrose, 5 g/L NaCl, 0.9 g/L dipotassium hydrogen phosphate trihydrate and water as solvent, pH=6.8.

Further, the pure enzyme is prepared as follows: the wet cells are suspended in a 0.2 M, pH 7.0 $Na_2HPO_4$—$NaH_2PO_4$ buffer, ultrasonic breaking is carried out under ice bath condition, the ultrasonic disrupter is set to the power of 40 W, 1 s breaking and 1 s pause, and the total breaking time is 20 min; then the resulting cell breaking solution is subjected to centrifugation at 12,000×g and 4° C. for 15 min, the cell debris is removed and the crude enzyme solution is collected; and the volume of the buffer calculated by the weight of the wet cells is 2 mL/g;

A Ni column is equilibrated with a binding buffer (Binding buffer: 50 mM $NaH_2PO_4$, 300 mM NaCl, 50 mM imidazole, pH 8.0) at a flow rate of 2 mL/min; then, the crude enzyme solution is loaded at a flow rate of 2 mL/min, and impurity proteins and weakly adsorbed proteins are eluted with a binding buffer at a flow rate of 2 mL/min; finally, the Ni column is eluted with an elution buffer (Elution buffer: 50 mM $NaH_2PO_4$, 300 mM NaCl, 500 mM imidazole, pH 8.0) at a flow rate of 3 mL/min, according to the UV parameters of the protein purifier (Bio-Rad BioLogic LP chromatography system), when UV≥2, the enzyme solution is collected, and when UV≤2, the collection is ended; then a dialysis bag (Shanghai labsee Biotechnology Co., Ltd.) is used for dialysis in a 50 mM $Na_2HPO_4$—$NaH_2PO_4$ (pH 7.0) buffer overnight, and the retentate is the pure nitrilase.

The method for preparing gabapentin from 1-cyanocyclohexyl acetic acid of the present invention is as follows:

(1) the conversion solution containing 1-cyanocyclohexyl acetic acid (1-CA) is subjected to centrifugation (8000 rpm, 10 min) to remove bacterial cells, the collected filtrate is 1-cyanocyclohexyl acetic acid, and the filtrate is placed in a hydrogenation reactor, Raney nickel (RTH-4110), triethylamine (analytical grade) and formic acid (analytical grade) are added; nitrogen is pumped in to replace the air and this operation is repeated 3 times to ensure that there is no air in the reactor; then hydrogen is pumped in again (the pressure of the reaction is maintained at 2 Mpa), and the reaction is carried out at 1000 rpm for 8 hours; and after cooling, the Raney nickel is recovered by filtration, and the resulting filtrate is added with isovolumetric dichloromethane for extraction, and after standing and stratification, the obtained organic phase is subjected to rotary evaporation at 40° C., the obtained solid is gabapentin-lactam, and the dichloromethane can be recycled for reuse; in which, the volume of the filtrate calculated by the weight of Raney nickel is 150 mL/1.5 g; the volume ratio of the triethylamine to the filtrate is 1:150; and the volumetric ratio of the formic acid to the filtrate is 0.5:150;

(2) the gabapentin-lactam obtained in step (1) is dissolved in a 6 M HCl solution and then subjected to heating reflux for 2.5 h, after cooling to room temperature, isovolumetric dichloromethane is added extraction, after standing and stratification, the obtained water phase is subjected to crystallization at 0-4° C. and suction filtration, the obtained white solid is ground with acetone and then subjected to filtration to remove the acetone and drying at 40° C. to obtain gabapentin hydrochloride; all the obtained gabapentin hydrochloride is dissolved in water, heated to 40° C. and stirred at 300 rpm to be fully dissolved, after the pH is adjusted to 7.0-7.5 by 6 M NaOH, toluene is added and stirred at 500 rpm for 30 min; and after the stirring, the mixture is subjected to crystallization at 0-4° C. and filtration to obtain the white solid which is crude gabapentin, and the crude gabapentin is subjected to heavy crystallization with 60% methanol or isopropanol and drying to obtain gabapentin. The volume of the HCl solution calculated by the weight of the gabapentin-lactam is 500 mL/76.7 g; the volume of the water which dissolves gabapentin hydrochloride calculated by the weight of the gabapentin-lactam is 500 mL/76.7 g; the volume of the toluene calculated by the weight of the gabapentin-lactam is 125 mL/76.7 g.

The present invention also provides an application of the recombinant enzyme containing the polypeptide tag in producing a clopidogrel intermediate (2-chloromandelic acid), wherein the application is carried out as follows: a reaction system is built using wet cells obtained from fermentation cultivation of the genetically engineered recombinant strain that contains the recombinant enzyme comprising the polypeptide tag (preferably recombinant nitrilase) as a catalyst, o-chloromandelonitrile as a substrate, and a pH=7.0, 0.2 M Na$_2$HPO$_4$—NaH$_2$PO$_4$ buffer as a reaction medium, the reaction is carried out in a constant temperature water bath at 35° C. for 12 h to obtain the reaction solution containing 2-chloromandelic acid, and the reaction solution is subjected to isolation and purification to obtain 2-chloromandelic acid. In the reaction system, the amount of the catalyst calculated by the weight of the wet cells is 50 g/L and the final concentration of the substrate is 1-2M.

The present invention also provides an application of the polypeptide tag recombinase in producing ECBN (Echinocandin B Nucleus), the application is as follows: a reaction system is built using wet cells obtained from fermentation cultivation of the genetically engineered recombinant strain that contains the recombinant enzyme (preferably deacylase (NC_001136.10)) comprising the polypeptide tag as a catalyst, Echinocandin B as a substrate, a pH=7.0, 0.2 M Na$_2$HPO$_4$—NaH$_2$PO$_4$ buffer and 1.5% β-cyclodextrin (as assistant solvent) as a reaction medium, the reaction is carried out in a constant temperature water bath at 35° C. for 24 h to obtain the mixture reaction solution containing unreacted substrates and partial products, and the mixture reaction solution is subjected to isolation and purification to obtain ECBN. In the reaction system, the amount of the catalyst calculated by the weight of the wet cells is 50 g/L and the final concentration of the substrate is 1-2M.

Compared with prior art, advantages of the present invention are mainly embodied in: the present invention provides a polypeptide tag, a recombinant nitrilase containing the polypeptide tag, application thereof in the synthesis of pharmaceutical chemicals such as gabapentin and the construction of the recombinant nitrilase by linking the polypeptide tag to the N-terminus of nitrilase. The polypeptide tag of the present invention is a positively charged tag. The polypeptide tag is added to the N-terminus of the nitrilase gene for fusion expression and construction of a recombinant strain, and the strain is subjected to induced expression for 12-14 h to obtain the whole cell catalyst. The activity of the whole cell catalyst used in the preparation of gabapentin intermediate1-cyanocyclohexyl acetic acid is up to 3034.7 U/g dcw, which means the polypeptide tag significantly improves the soluble expression of nitrilase, and the whole cell catalyst hydrolyzes 1M substrate with the same concentration 30 minutes faster than the mother enzyme, and the stability of it is better than the mother enzyme. The method provided by the present invention can also be used for the biocatalytic reaction of other pharmaceutical intermediates as the substrate catalyzed by the nitrilase, improving the activity of the whole cell catalyst in reaction, and also improving the solubility of other types of nitrilases or other enzymes and the activity of the corresponding whole cell catalysts.

SPECIFIC EMBODIMENTS

Figure 1:
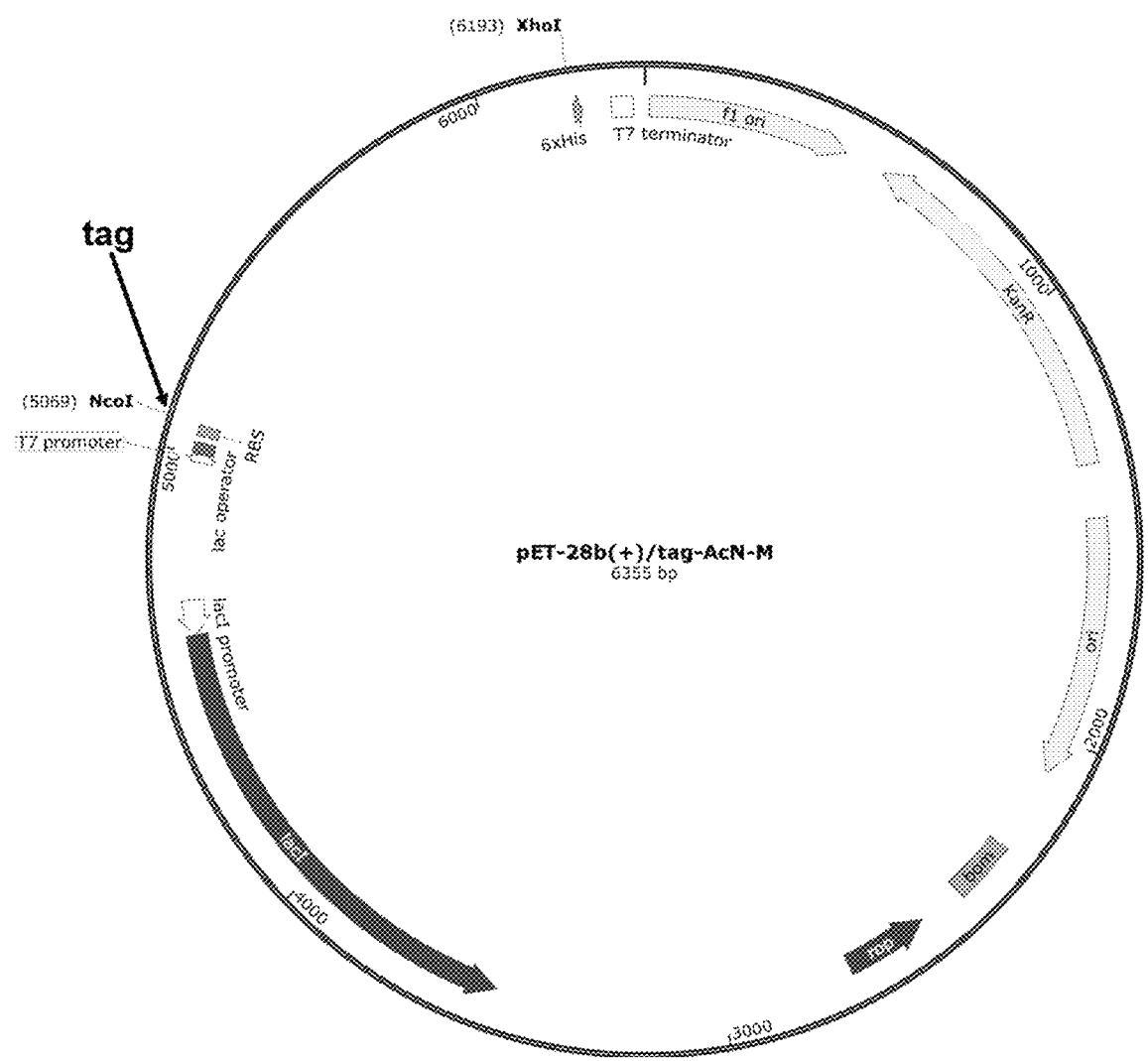
FIG. 1: A schematic map of the recombinant plasmid pET-28b+/tag-AcN-M with the polypeptide tag.
Figure 2:
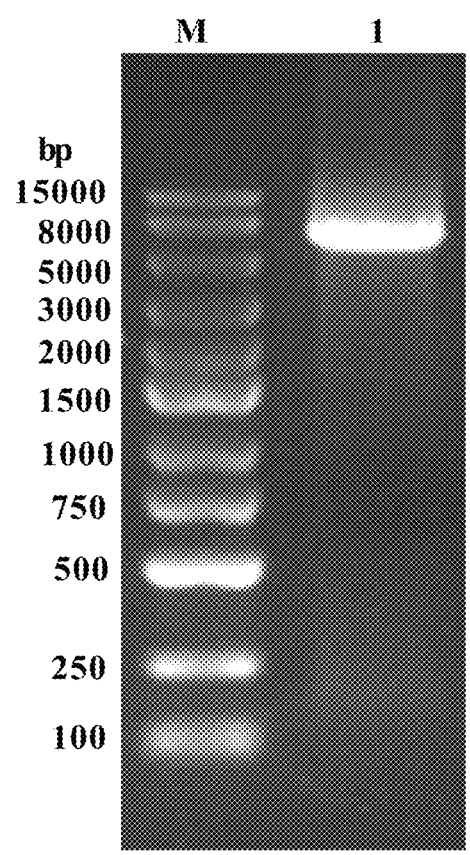
FIG. 2: Nucleic acid gel electrophoresis diagram, lane M is Maker, lane 1 is the product of full-length plasmid PCR.

The present invention is further illustrated below with specific examples, but the scope of the present invention is not limited thereto:

The medium involved in the following examples are as follows:

Mass composition LB of solid medium: 5 g/L yeast powder, 10 g/L peptone, 10 g/L NaCl, 2% agar powder, the solvent is water, pH=7.0.

LB liquid medium: 5 g/L yeast powder, 10 g/L peptone, 10 g/L NaCl, the solvent is water, pH=7.0.

Fermentation medium: 20 g/L yeast powder, 15 g/L sucrose, 5 g/L NaCl, 0.9 g/L dipotassium hydrogen phosphate trihydrate, the solvent is water, pH=6.8.

The detection methods involved in the following examples are as follows:

The definition of enzyme activity: under certain conditions, the amount of enzyme required to catalyze the production of 1 μmol of 1-cyanocyclohexyl acetic acid (1-CA) from the substrate per minute is defined as one unit of activity, denoted as U.

Specific enzyme activity refers to the number of enzyme activity units per unit weight (mg) of protein under certain conditions.

Determination method of the activity of resting cells: 0.01 g of resting cells is suspended in 1 mL of 0.2 M, pH 7.0 $Na_2HPO_4$—$NaH_2PO_4$ buffer and incubated at 35° C. for 10 min, 0.03 g of substrate 1-cyanocyclohexylacetonitrile (1-CN) (final concentration of 0.2 M) is added, the resulting mixture is subjected to shaking reaction at 200 rpm and 35° C. constant temperature for 10 minutes, after the reaction, the resulting reaction solution is subjected to centrifugation at 12,000 rpm for 5 minutes, and the supernatant is taken to determine the product concentration.

The specific enzyme activity of the original strain under the standard enzyme activity determination conditions is set as 100%, and the ratio of the specific enzyme activity of the recombinant strain to the specific enzyme activity of the original strain is the relative cell activity (%).

Substrate 1-CN concentration detection method: gas chromatography: Agilent 7890A, chromatographic column: Agilent J&WHP-5 Column (30 m×0.32 mm, film thickness 0.25 μm), the temperatures of injection port and detector are set up as 320° C.; the temperature of column is set up as 160° C. for 8 min; carrier gas: high-purity helium; carrier gas flow: 1.0 mL/min; injection volume: 1 μL; split ratio is 30:1.

Product 1-CA concentration detection method: liquid chromatography: chromatographic column type is C18-H, 250 mm×4.6 mm, J&K Scientific Ltd., China; chromatographic conditions are column temperature at 40° C., UV detection wavelength at 215 nm and mobile phase as 76% buffer (0.58 g/L $NH_4H_2PO_4$ and 1.83 g/L $NaClO_4$, pH 1.8) and 24% acetonitrile.

The nitrilase gene was cloned from *Acidovorax facilis* (*Acidovorax facilis* ZJB09122), and the amino acid sequence is shown in SEQ ID NO: 1 and the nucleotide sequence is shown in SEQ ID NO: 2. The *Acidovorax facilis* (*Acidovorax facilis* ZJB09122) is deposited in the China Center for Type Culture Collection, and the deposit number is CCTCC NO.M209044, which has been disclosed in the patent CN101629192B.

Example 1: Construction of a Recombinant Plasmid Containing a Polypeptide Tag

1. The design principle is as follows: the solubility of a protein is closely related to the hydrophobicity of the residues, and it is also affected by the net charge of the protein or the proportion of helical residues. Polar amino acids have an important influence on the solubility of proteins. The palindrome element sequence is usually composed of multiple repeating units containing one or two polar amino acids, with positive or negative charge, and it has been reported that it can promote protein folding, and is usually less than 15 residues.

Based on the above principles, we first designed a pentapeptide tag, in which amino acids at both ends and the middle (ie amino acids at position 1, 3, 5) are uncharged glycine (G), and the rest (ie amino acids at position 2, 4) are a random combination of any one or more of glycine (G), histidine (H), glutamic acid (E), aspartic acid (D), lysine (K), arginine (R), specifically one of the following: GDGDG (SEQ ID NO: 9), GDGEG(SEQ ID NO: 10), GDGRG(SEQ ID NO: 11), GDGKG(SEQ ID NO: 12), GDGGG(SEQ ID NO: 35), GEGEG(SEQ ID NO: 13), GEGKG(SEQ ID NO: 14), GEGGG(SEQ ID NO: 15), GEGRG(SEQ ID NO: 16), GEGDG(SEQ ID NO: 17), GKGKG(SEQ ID NO: 3), GKGDG(SEQ ID NO: 18), GKGEG(SEQ ID NO: 4), GKGGG(SEQ ID NO: 19), GKGHG(SEQ ID NO: 5), GKGRG(SEQ ID NO: 20), GRGRG(SEQ ID NO: 6), GRGDG(SEQ ID NO: 21), GRGEG(SEQ ID NO: 22), GRGKG(SEQ ID NO: 23), GRGGG(SEQ ID NO: 7), GGGEG(SEQ ID NO: 25), GHGHG(SEQ ID NO: 8) and GGGKG(SEQ ID NO: 24).

Secondly, the linker peptide was designed, and the amino acid sequence is one of the following: GS, GGS, GGGS (SEQ ID NO: 29), or GGGGS(SEQ ID NO: 30).

Finally, a polypeptide tags with an extended peptide chain and the polypeptide tags containing linker peptides are designed: GKGKGKG (SEQ ID NO: 26), GKGKGKGKG (SEQ ID NO: 27), GKGKGKGKGKG (SEQ ID NO: 28), GKGKG-GS(SEQ ID NO: 31), GKGKG-GGS(SEQ ID NO: 32), GKGKG-GGGS(SEQ ID NO: 33), or GKGKG-GGGGS(SEQ ID NO: 34).

2. According to the patent application (CN104212784A), the recombinant *E. coli* BL21(DE3)/pET28b(+)-AcN2 containing the expression vector pET-28b(+) was obtained from *Acidovorax facilis* (*Acidovorax facilis* ZJB09122), and then according to the patent application (CN107177576A) *E. coli* BL21(DE3)/pET28b(+)-AcN-T151V/C223A/C250G was prepared.

The recombinant plasmid pET28b(+)-AcN-T151V/C223A/C250G was extracted from *E. coli* BL21(DE3)/pET28b(+)-AcN-T151V/C223A/C250G, which was the recombinant plasmid pET-28b(+)/AcN-M, wherein the nucleotide sequence of AcN-M was shown in SEQ ID NO:2, and the amino acid sequence was shown in SEQ ID NO:1.

The recombinant plasmid pET-28b(+)/AcN-M containing the encoding gene of the nitrilase (AcN-M) shown in SEQ ID NO:1 as the template and the forward and reverse primers containing the polypeptide tag in step 1 were used to carry out PCR amplification and the polypeptide tag designed in step 1 was directly linked to the N-terminal of the nitrilase gene through PCR amplification, the PCR amplification product was subjected to gel electrophoresis to verify the success of the PCR, and then dpn I was added in the amount of 1 μL/50 μL amplification system and reacted at 37° C. for 30 min to digest the template, 25 μL of the resulting reaction solution was taken for sequencing verification (Hangzhou tsingke Biological Technology Co., Ltd.), and the PCR product containing the recombinant plasmid ET-28b(+)/tag-AcN-M was obtained, shown in table 1, tag represented the polypeptide tag.

The PCR system was as follows: 25 μL of 2×Phanta Max Buffer (PCR system buffer), 1 μL of d NTP Mix (dATP, dCTP, dGTP, dTTP), 1 μL of the template, 1 μL of the forward primer, 1 μL of the reverse primer, 1 μL of Phanta Max Super-Fidelity DNA Polymerase (High-fidelity Thermostable DNA Polymerase), 20 μL of dd H2O, 50 μL in total.

The PCR reaction conditions were: pre-denaturation at 95° C. for 5 min; 30 cycles: denaturation at 95° C. for 30 seconds, annealing at 55-65° C. for 1 min, extension at 72° C. for 5.5 min and 72° C. for 10 min.

TABLE 1

Primers containing the peptide tags

| Name of the primers | Amino acid sequence |
|---|---|
| T7 | TAATACGACTCACTATAGGG (SEQ ID NO: 36) |
| T7 ter | TGCTAGTTATTGCTCAGCGG (SEQ ID NO: 37) |
| GDGDG-F | ACCATGGGTGATGGTGATGGTGTATCTTACAACTCC (SEQ ID NO: 38) |
| GDGDG-R | GTAAGATACACCATCACCATCACCCATGGTATATCTCC (SEQ ID NO: 39) |
| GDGEG-F | ACCATGGGTGATGGTGAAGGTGTATCTTACAACTCC (SEQ ID NO: 40) |
| GDGEG-R | GTAAGATACACCTTCACCATCACCCATGGTATATCTCC (SEQ ID NO: 41) |
| GDGRG-F | TACCATGGGTGATGGTCGAGGTGTATCTTACAACTCC (SEQ ID NO: 42) |
| GDGRG-R | GATACACCTCGACCATCACCCATGGTATATCTCCTTCT (SEQ ID NO: 43) |
| GDGKG-F | TACCATGGGTGATGGTAAAGGTGTATCTT (SEQ ID NO: 44) |
| GDGKG-R | GAAATTTGGAGTTGTAAGATACACCATCACC (SEQ ID NO: 45) |
| GDGGG-F | TACCATGGGTGATGGTGGTGGTGTATCTT (SEQ ID NO: 46) |
| GDGGG-R | GAAATTTGGAGTTGTAAGATACACCACCACC (SEQ ID NO: 47) |
| GEGEG-F | CATGGGTGAAGGTGAAGGTGTATCT (SEQ ID NO: 48) |
| GEGGE-R | ACCTTCACCTTCACCCATGGTATA (SEQ ID NO: 49) |
| GEGKG-F | CATGGGTGAAGGTGAAGGTGTATCT (SEQ ID NO: 50) |
| GEGKG-R | ACCTTCACCTTCACCCATGGTATA (SEQ ID NO: 51) |
| GEGGG-F | TACCATGGGTGAAGGTGGTGGTGTATCT (SEQ ID NO: 52) |
| GEGGG-R | AGTTGTAAGATACACCACCACCTTCACCCATG (SEQ ID NO: 53) |
| GEGRG-F | TACCATGGGTGAAGGTCGAGGTGTATCT (SEQ ID NO: 54) |
| GEGRG-R | AGTTGTAAGATACACCTCGACCTTCACCCATG (SEQ ID NO: 55) |
| GEGDG-F | CATGGGTGAAGGTGATGGTGTATCT (SEQ ID NO: 56) |
| GEGDG-R | ACCATCACCTTCACCCATGGTATA (SEQ ID NO: 57) |
| GKGKG-F | GGTAAAGGTAAAGGTGTATCTTACAACT (SEQ ID NO: 58) |
| GKGKG-R | TACACCTTTACCTTTACCCATGG (SEQ ID NO: 59) |
| GKGDG-F | ACCATGGGTAAAGGTGATGGTGTATCTTACAACTCC (SEQ ID NO: 60) |
| GKGDG-R | GTAAGATACACCATCACCTTTACCCATGGTATATCTCC (SEQ ID NO: 61) |
| GKGEG-F | ACCATGGGTAAAGGTGAAGGTGTATCTTACAACTCC (SEQ ID NO: 62) |
| GKGEG-R | GTAAGATACACCTTCACCTTTACCCATGGTATATCTCC (SEQ ID NO: 63) |
| GKGGG-F | TACCATGGGTAAAGGTGTTGGTGTATCTTACAAC (SEQ ID NO: 64) |

TABLE 1-continued

Primers containing the peptide tags

| Name of the primers | Amino acid sequence |
|---|---|
| GKGGG-R | TACACCAACACCTTTACCCATGGTATATCTCCTT (SEQ ID NO: 65) |
| GKGHG-F | TACCATGGGTAAAGGTCACGGTGTATCTTACAACTCCA (SEQ ID NO: 66) |
| GKGHG-R | GATACACCGTGACCTTTACCCATGGTATATCTCCTT (SEQ ID NO: 67) |
| GKGRG-F | TACCATGGGTAAAGGTCGAGGTGTATCTTACAACTCCA (SEQ ID NO: 68) |
| GKGRG-R | GATACACCTCGACCTTTACCCATGGTATATCTCCTT (SEQ ID NO: 69) |
| GRGRG-F | TACCATGGGTCGAGGTCGAGGTGTATCTTACAACTCC (SEQ ID NO: 70) |
| GRGRG-R | GATACACCTCGACCTCGACCCATGGTATATCTCCTTCT (SEQ ID NO: 71) |
| GRGDG-F | ACCATGGGTCGTGGTGATGGTGTATCTTACAAC (SEQ ID NO: 72) |
| GRGDG-R | ATACACCATCACCACGACCCATGGTAATCTCC (SEQ ID NO: 73) |
| GRGEG-F | ACCATGGGTCGTGGTGAAGGTGTATCTTACAAC (SEQ ID NO: 74) |
| GRGEG-R | ATACACCTTCACCACGACCCATGGTAATCTCC (SEQ ID NO: 75) |
| GRGKG-F | TACCATGGGTCGAGGTAAAGGTGTATCTTACAACTCCA (SEQ ID NO: 76) |
| GRGKG-R | GATACACCTTTACCTCGACCCATGGTATATCTCCTT (SEQ ID NO: 77) |
| GRGGG-F | ACCATGGGTCGTGGTGGTGGTGTATCTTACAAC (SEQ ID NO: 78) |
| GRGGG-R | ATACACCACCACCACGACCCATGGTAATCTCC (SEQ ID NO: 79) |
| GGGKG-F | TACCATGGGTGGTGGTAAAGGTGTATCTT (SEQ ID NO: 80) |
| GGGKG-R | GAAATTTGGAGTTGTAAGATACACCTTTACC (SEQ ID NO: 81) |
| GGGEG-F | TACCATGGGTGGTGGTGAAGGTGTAT (SEQ ID NO: 82) |
| GGGEG-R | TTGTAAGATACACCTTCACCACCACCCAT (SEQ ID NO: 83) |
| GHGHG-F | TACCATGGGTCACGGTCACGGTGTATCTTACAACTCCA (SEQ ID NO: 84) |
| GHGHG-R | GATACACCGTGACCGTGACCCATGGTATATCTCCTT (SEQ ID NO: 85) |
| GKGKGKG-F | ACCATGGGTAAAGGTAAAGGTAAAGGTGTATCTTACA (SEQ ID NO: 86) |
| GKGKGKG-R | TGGAGTTGTAAGATACACCTTTACCTTTACCTTTA (SEQ ID NO: 87) |
| GKGKGKGKG-F | ACCATGGGTAAAGGTAAAGGTAAAGGTAAAGGTGTATCTTAC (SEQ ID NO: 88) |
| GKGKGKGKG-R | TGGAGTTGTAAGATACACCTTTACCTTTACCTTTACCTTTA (SEQ ID NO: 89) |

TABLE 1-continued

Primers containing the peptide tags

| Name of the primers | Amino acid sequence |
|---|---|
| GKGKGKGKGKG-F | ACCATGGGTAAAGGTAAAGGTAAAGGTAAAGGTAAAGGTGT<br>ATCTTAC (SEQ ID NO: 90) |
| GKGKGKGKGKG-R | TAAAGGTAAAGGTGGTTCTGTATCTTACAACTCCAAGATACA<br>GAACCACCTTTACCTTTACCCATG (SEQ ID NO: 91) |
| GKGKG-GS-F | TAAAGGTAAAGGTGGTTCTGGTTCTGTATCTTACAACTCCA<br>(SEQ ID NO: 92) |
| GKGKG-GS-R | AGATACAGAACCAGAACCACCTTTACCTTTACCCATG<br>(SEQ ID NO: 93) |
| GKGKG-GGS-F | TAAAGGTAAAGGTGGTGGTTCTGTATCTTACAACTCCA<br>(SEQ ID NO: 94) |
| GKGKG-GGS-R | AGATACAGAACCACCACCTTTACCTTTACCCATG<br>(SEQ ID NO: 95) |
| GKGKG-GGGS-F | TAAAGGTAAAGGTGGTGGTGGTTCTGTATCTTACAACTCCA<br>(SEQ ID NO: 96) |
| GKGKG-GGGS-R | AGATACAGAACCACCACCACCTTTACCTTTACCCATG<br>(SEQ ID NO: 97) |
| GKGKG-GGGGS-F | TAAAGGTAAAGGTGGTGGTGGTGGTTCTGTATCTTACAACTC<br>(SEQ ID NO: 98) |
| GKGKG-GGGGS-R | AGATACAGAACCACCACCACCACCTTTACCTTTACCCATG<br>(SEQ ID NO: 99) |

Example 2: Construction of the Recombinant E. coli

Axygen clean-up kit (purchased from Corning Life Sciences (Wujiang) Co. Ltd.) was used to purify (clean-up) the PCR product containing the recombinant plasmid pET-28b (+)/tag-AcN-M in Example 1, and the specific operations were as follows: 5 μL of the PCR product in Example 1 was added with three sample volumes of PCR-A buffer, mixed thoroughly, transferred to the preparation tube, and subjected to centrifugation at 12000 rpm for 1 min, the filtrate was discard, and 700 μL of W2 buffer was added to the preparation tube, the resulting mixture was subjected to centrifugation at 12000 rpm for 1 min, the filtrate was discard and a W2 buffer was used to wash the leftover twice; pre-thawed competent cells E. coli BL21(DE3) was added with 5 μL of the product, kept in ice bath for 30 min, subjected to heat shock at 42° C. for 90 s, kept in ice bath for 3-5 min again, added with 700 μL of LB liquid medium, and incubated at 37° C. for 1 h. 500 μL of the resulting inoculum was inoculated to LB solid medium containing 0.5 μg/mL kanamycin, spread evenly and incubated at 37° C. for 12-14 h, the single colonies was picked for sequencing verification, thereby obtaining the recombinant E. coli BL21 (DE3)/pET-28b(+)/tag-AcN-M. Under the same conditions, the original strain E. coli BL21(DE3)/pET-28b(+)/AcN-M was constructed.

Example 3: Expression of Nitrilase in the Recombinant Escherichia coli

1. Resting cells: the recombinant E. coli BL21(DE3)/pET-28b(+)/tag-AcN-M strain constructed in Example 2 and stored at −80° C. in a refrigerator was taken out and inoculated into LB medium containing 0.5 μg/mL kanamycin and cultivated at 37° C. for 12-14 h hours to obtain single colonies; a single colony was picked, inoculated to 10 mL of LB medium containing 0.5 μg/mL kanamycin, and cultivated at 37° C. for 8 h, 2 mL of the resulting inoculum was inoculated to 100 mL of fermentation medium containing 0.5 μg/mL kanamycin and cultivated at 37° C. for 2 h, and then 100 μL of IPTG was added (the final concentration was 0.1 mM), and the bacteria solution was induced to produce the enzyme at 28° C. for 12-14 h and subjected to centrifugation at 12,000 rpm for 10 min, the collected wet cells was washed with 0.9% saline twice to obtain the resting cell suspension, and the relative enzyme activity was determined.

2. Pure enzyme: 1 g of the resting cells obtained by the method in step 1 were suspended in 10 mL of 0.2 M, pH 7.0 Na$_2$HPO$_4$—NaH$_2$PO$_4$ buffer, ultrasonic breaking was carried out under ice bath condition, the ultrasonic disrupter was set to the power of 40 W, 1 s breaking and 1 s pause, and the total breaking time is 20 min. Then the resulting cell breaking solution was subjected to centrifugation at 12,000×g and 4° C. for 15 min, the cell debris was removed and the crude enzyme solution was collected; a BCA kit was used to detect the protein content, which is the total protein content.

A Ni column was equilibrated with a binding buffer (Binding buffer: 50 mM NaH$_2$PO$_4$, 300 mM NaCl, 50 mM imidazole, pH 8.0) at a flow rate of 2 mL/min. Then, the crude enzyme solution was loaded at a flow rate of 2 mL/min, and impurity proteins and weakly adsorbed proteins were eluted with a binding buffer at a flow rate of 2 mL/min. Finally, the Ni column was eluted with an elution buffer (Elution buffer: 50 mM NaH$_2$PO$_4$, 300 mM NaCl, 500 mM imidazole, pH 8.0) at a flow rate of 3 mL/min, according to the UV parameters of the protein purifier (Bio-Rad BioLogic LP chromatography system), when UV≥2, the enzyme solution was collected, and when UV≤2, the collection was ended. Then a dialysis bag (Shanghai labsee Biotechnology Co., Ltd.) was used for dialysis in a 50 mM $Na_2HPO_4$—$NaH_2PO_4$(pH 7.0) buffer overnight, and the retentate was the pure nitrilase and it was stored in an ice bath for use. A BCA kit was used to detect the protein content, which was the protein content of the supernatant.

Solubility (%)=supernatant protein amount/total protein amount×100%.

TABLE 2

Comparison of relative enzyme activity and solubility of the recombinant strains containing different peptide tags

| Tags | Relative cell enzyme activity (%) | Solubility (%) |
|---|---|---|
| AcN-M | 100 | 53.6 |
| GDGDG (SEQ ID NO: 9) | 55.8 | 60.6 |
| GDGEG (SEQ ID NO: 10) | 50.9 | 60.8 |
| GDGRG (SEQ ID NO: 11) | 25.0 | 60.1 |
| GDGKG (SEQ ID NO: 12) | 35.9 | 70.9 |
| GDGGG (SEQ ID NO: 35) | 19.0 | 62.1 |
| GEGEG (SEQ ID NO: 13) | 18.3 | 68.8 |
| GEGKG (SEQ ID NO: 14) | 72.6 | 84.7 |
| GEGGG (SEQ ID NO: 15) | 5.5 | 74.6 |
| GEGRG (SEQ ID NO: 16) | 64.5 | 83.4 |
| GEGDG (SEQ ID NO: 17) | 45.6 | 60.8 |
| GKGKG (SEQ ID NO: 3) | 237.3 | 87.9 |
| GKGDG (SEQ ID NO: 18) | 32.9 | 70.9 |
| GKGEG (SEQ ID NO: 4) | 154.1 | 84.7 |
| GKGGG (SEQ ID NO: 19) | 40.5 | 75.8 |
| GKGHG (SEQ ID NO: 5) | 109.6 | 87.5 |
| GKGRG (SEQ ID NO: 20) | 103.6 | 87.6 |
| GRGRG (SEQ ID NO: 6) | 115.6 | 86.7 |
| GRGDG (SEQ ID NO: 21) | 23.0 | 60.1 |
| GRGEG (SEQ ID NO: 22) | 60.5 | 83.4 |
| GRGKG (SEQ ID NO: 23) | 65.5 | 82.4 |
| GRGGG (SEQ ID NO: 7) | 101.6 | 84.7 |
| GGGKG (SEQ ID NO: 24) | 18.4 | 70.4 |
| GGGEG (SEQ ID NO: 25) | 0 | 74.6 |
| GHGHG (SEQ ID NO: 8) | 108.2 | 83.8 |

Figure 3:
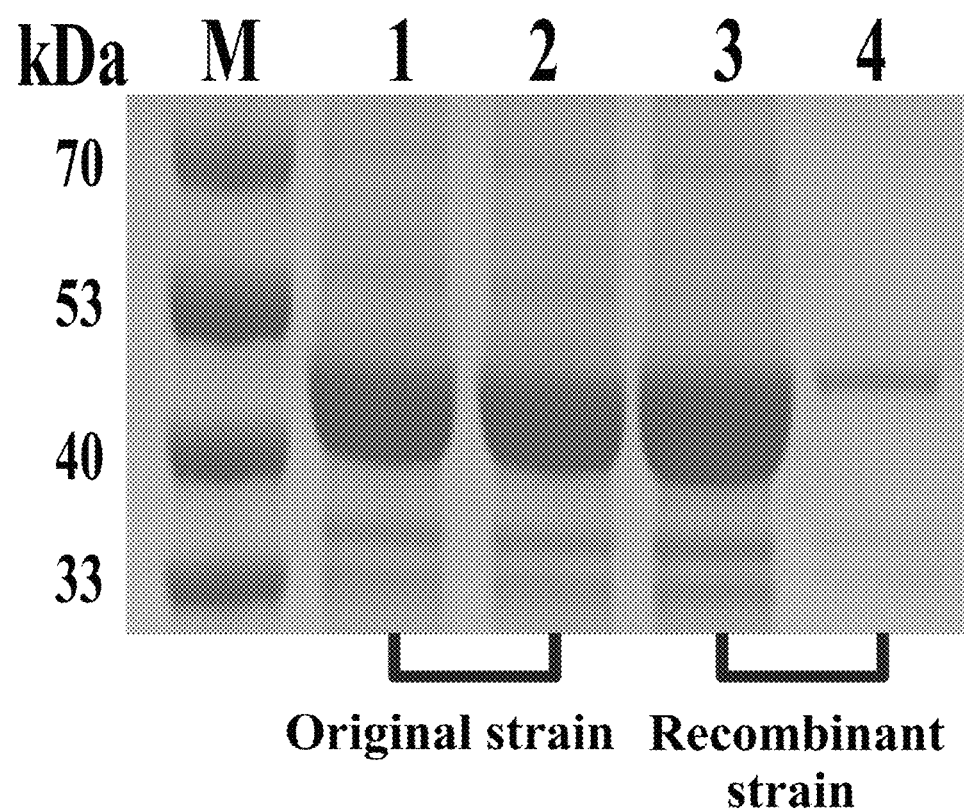
FIG. 3: SDS-PAGE electrophoresis diagram of cell breaking supernatant and precipitation samples of the recombinant strain *E. coli* BL21(DE3)/pET-28b(+)/GKGKG (SEQ ID NO: 3)-AcN-M; wherein M is protein molecular weight makers, 1 and 2 are the cell breaking supernatant and precipitation of the original strain, respectively; 3 and 4 are cell breaking supernatant and precipitation of the recombinant strain, respectively.

According to Table 2, the relative enzyme activity results showed that the enzyme activity of recombinant E. coli BL21(DE3)/pET-28b(+)/GKGKG(SEQ ID NO: 3)-AcN-M is 2.37 times that of the original strain, and the insertion of the tag hardly affected the normal growth of the recombinant E. coli. The protein electrophoresis experiment was shown in FIG. 3, the soluble expression (supernatant protein amount/total protein amount) of the recombinant strain was significantly enhanced, the solubility of the original strain was only 53.6%, whereas the solubility of the recombinant strain reached 87.9%.

4. The effect of the length of the polypeptide tag sequence on the solubility of the enzymes of the original strain and the recombinant strain E. coli BL21(DE3)/pET-28b(+)/tag-AcN-M

TABLE 3

Comparison of relative enzyme activity and solubility of recombinant strains containing polypeptide tags with different lengths

| Tag | Relative cell enzyme activity (%) | Solubility (%) |
|---|---|---|
| AcN-M | 100 | 53.6 |
| GKGKG (SEQ ID NO: 3) | 237.3 | 87.9 |
| GKGKGKG (SEQ ID NO: 26) | 222.9 | 90.9 |
| GKGKGKGKG (SEQ ID NO: 27) | 111.4 | 88.6 |
| GKGKGKGKGKG (SEQ ID NO: 28) | 35.9 | 86.8 |

According to Table 3, the influence of the polar amino acids in the polypeptide tags on the solubility was more obvious. The solubility of the nitrilase with the polypeptide tag containing 3 lysine residues reached 90.9%, while the solubility of the nitrilase with tags in other length did not change dramatically.

5. The effect of the linker between the polypeptide tag and the target gene on the solubility of the original strain and the recombinant strain *E. coli* BL21(DE3)/pET-28b(+)/tag-AcN-M

TABLE 4

Comparison of relative enzyme activity and solubility of recombinant strains containing different linkers

| Linker | Relative cell enzyme activity (%) | Solubility (%) |
|---|---|---|
| GKGKG (SEQ ID NO: 3) | 237.3 | 87.9 |
| GKGKG-GS (SEQ ID NO: 31) | 219.6 | 67.3 |
| GKGKG-GGS (SEQ ID NO: 32) | 150.5 | 70.5 |
| GKGKG-GGGS (SEQ ID NO: 33) | 90.2 | 80.4 |
| GKGKG-GGGGS (SEQ ID NO: 34) | 59.6 | 89.1 |

According to Table 4, the linkers played an very important role in polypeptide tags and target genes. The longer the linker was, the higher the solubility of nitrilase was, but the stronger the inhibitory effect on its catalytic activity was. And the catalytic activity of the recombinant strain cells which contained the polypeptide tag combined with the longest linker was as low as 59.6%.

According to Table 2 to Table 4, the recombinant strain *E. coli* BL21(DE3)/pET-28b(+)/GKGKG(SEQ ID NO: 3)-AcN-M was selected for subsequent experiments.

Figure 4:
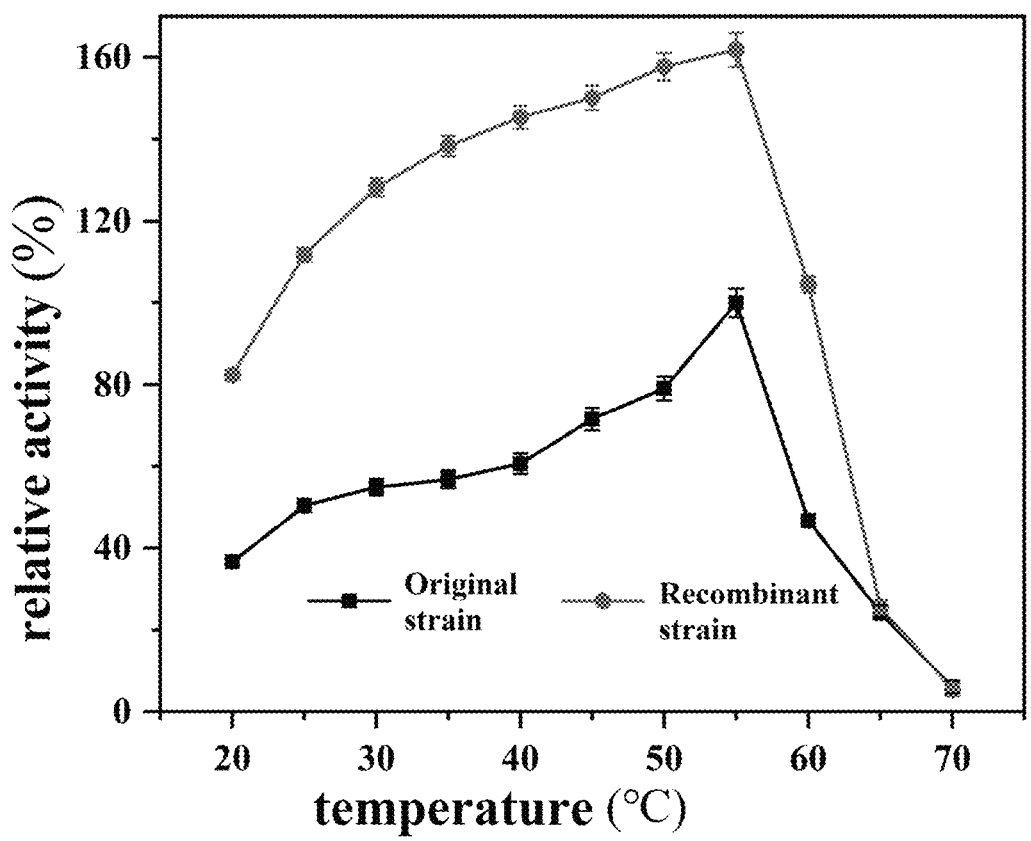
FIG. 4: Comparison of the relative enzyme activity of the original strain and the recombinant strain *E. coli* BL21 (DE3)/pET-28b(+)/GKGKG(SEQ ID NO: 3)-AcN-M at different temperatures; wherein the activity value of the original strain under standard enzyme activity determination conditions is set as 100%.

Example 4: Effect of Temperature on Cell Enzyme Activity of the Original Strain and the Recombinant Strain *E. coli* BL21(DE3)/pET-28b(+)/GKGKG(SEQ ID NO: 3)-AcN-M 1 ml of a reaction system was constructed by mixing 900 μL of 200 mM, pH 7.0 $Na_2HPO_4$—$NaH_2PO_4$ buffer with 100 μL of the resting cell suspension prepared by the method in Example 3 to make the amount of the resting cells added to the reaction system was 10 g/L, maintained on an oscillation reactor for 10 minutes at a set temperatures of 20° C., 25° C., 30° C., 35° C., 40° C., 45° C., 50° C., 55° C., 60° C., 65° C. and 70° C., respectively, added with 1-CN with the final concentration of 0.2 M, and reacted on the oscillation reactor at 800 rpm for 10 minutes. Then the sample was subjected to centrifugation, the supernatant was picked, and the concentration of 1-CA in the supernatant was analyzed by HPLC. Under the same conditions, with the original strain *E. coli* BL21(DE3)/pET-28b(+)/AcN-M as a control, the results were shown in FIG. 4, the optimal temperature for the recombinant strain was 55° C., which is the same as the original strain, and at the same temperature, the cell enzyme activity of the recombinant strain was higher than that of the original strain.

Figure 5:
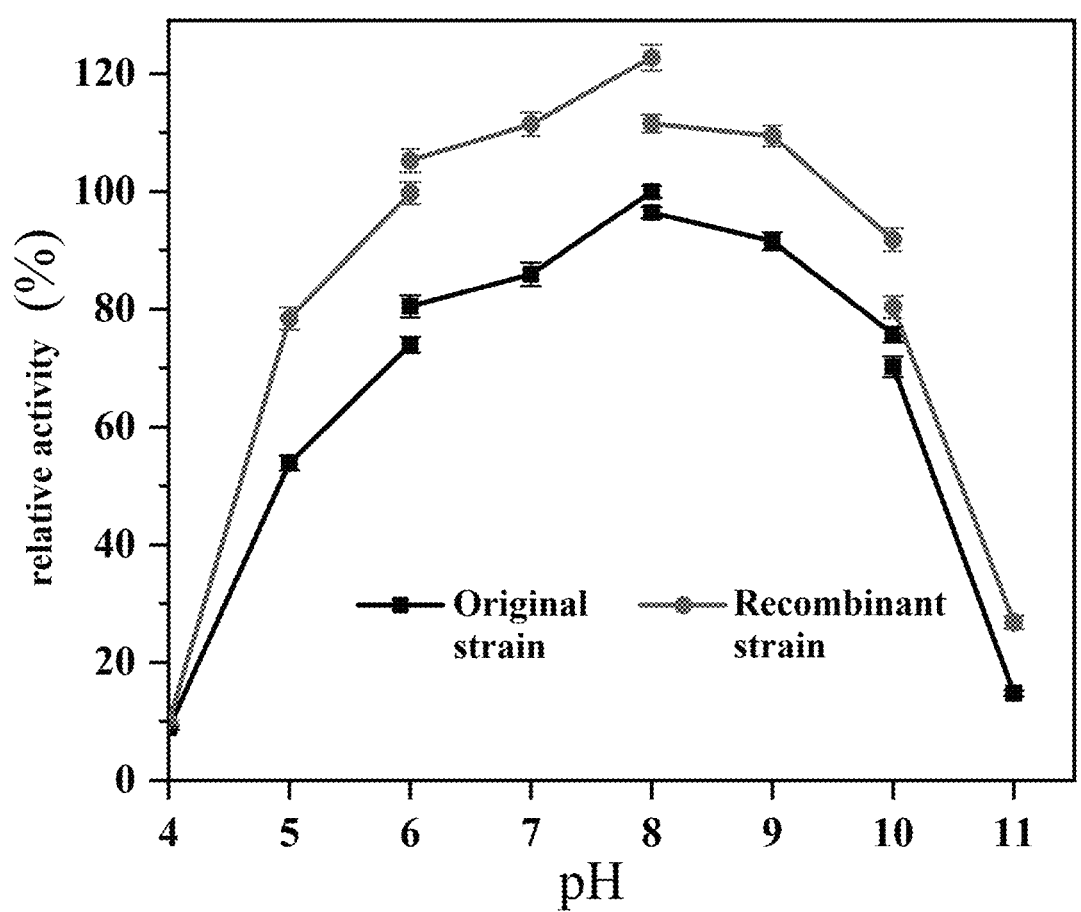
FIG. 5: Comparison of the relative enzyme activity of the original strain and the recombinant strain *E. coli* BL21 (DE3)/pET-28b(+)/GKGKG(SEQ ID NO: 3)-AcN-M under different pHs; wherein the activity value of the original strain under standard enzyme activity determination conditions is set as 100%.

Example 5: Effect of pH on Cell Enzyme Activity of the Original Strain and the Recombinant Strain *E. coli* BL21(DE3)/pET-28b(+)/GKGKG(SEQ ID NO: 3)-AcN-M 1 mL of a reaction system was constructed by adding 900 μL of buffers with different pH values (0.1 M, pH 4.0-6.0 citric acid-sodium citrate buffer; 0.2 M, pH 6.0-8.0 $Na_2HPO_4$—$NaH_2PO_4$ buffer) to 100 μL of the resting cell suspension prepared by the method in Example 3 to make the amount of the resting cells added to the reaction system was 10 g/L, preheated on an oscillation reactor for 10 minutes at 35° C., added with 1-CN with the final concentration of 0.2 M, and reacted at 800 rpm for 10 minutes. Then the sample was subjected to centrifugation at 12,000 rpm for 5 min, the supernatant was picked, and the concentration of 1-CA in the supernatant was analyzed by HPLC. Under the same conditions, with the original strain *E. coli* BL21(DE3)/pET-28b(+)/AcN-M as a control, the results were shown in FIG. 5, the optimal pH for the recombinant strain was 8.0, which is the same as the original strain, and at the same pH, the cell enzyme activity of the recombinant strain was higher than that of the original strain.

Figure 6A:
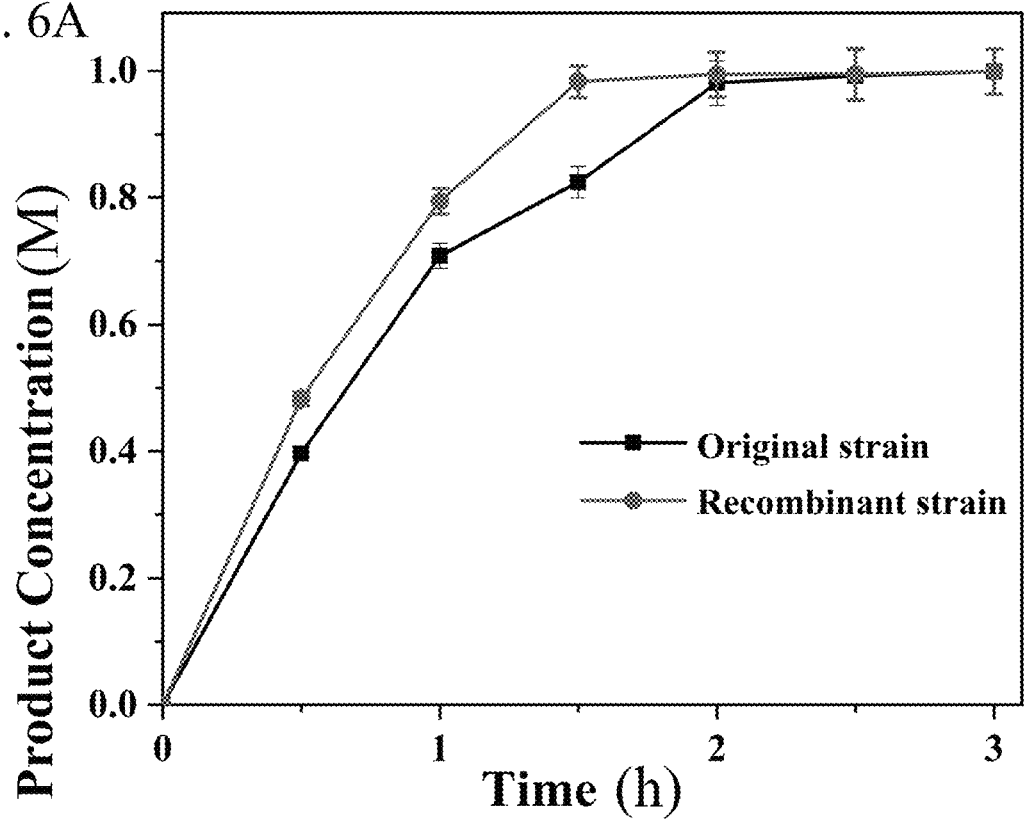
FIG. 6: Comparison of the accumulation concentration of catalytic products between the original strain and the recombinant strain *E. coli* BL21(DE3)/pET-28b(+)/GKGKG(SEQ ID NO: 3)-AcN-M at different substrate concentrations, wherein the substrate concentration of A is 1M, and the substrate concentration of B is 2M.
Figure 6B:
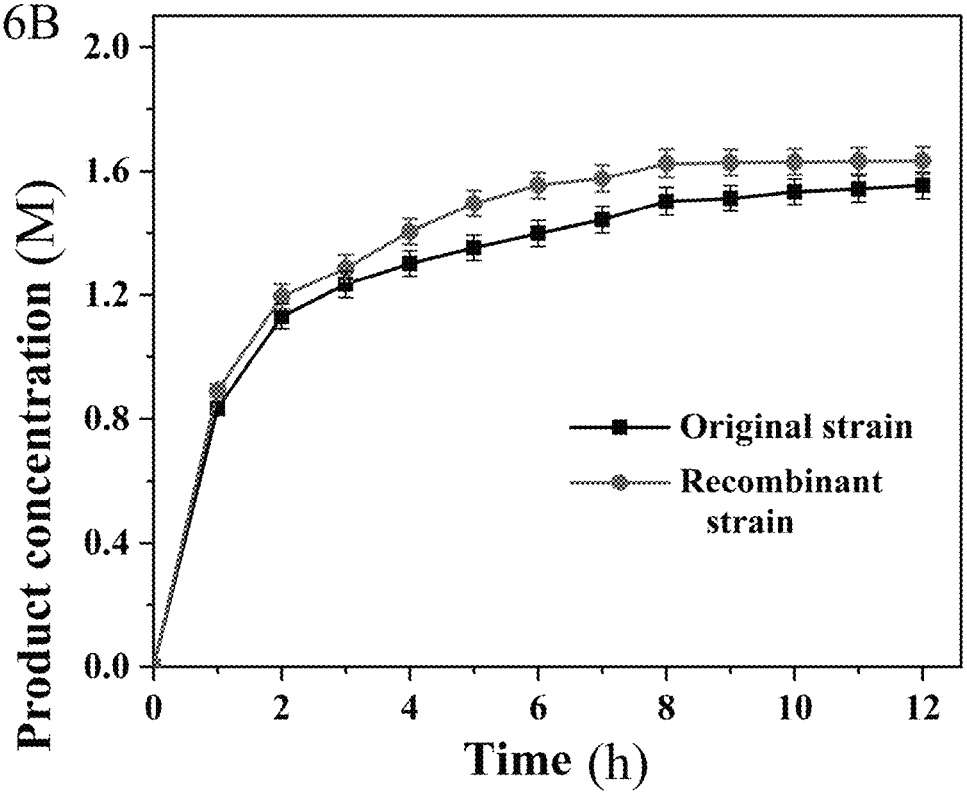

Example 6: Comparison of the Cell Catalytic Efficiency of the Original Strain and the Recombinant Strain *E. coli* BL21(DE3)/pET-28b(+)/GKGKG(SEQ ID NO: 3)-AcN-M 5 g of the wet cells of recombinant *E. coli* BL21(DE3)/pET-28b(+)/GKGKG(SEQ ID NO: 3)-AcN-M prepared by the method of Example 3 were suspended in 100 mL of $Na_2HPO_4$—$NaH_2PO_4$ buffer (0.2 M, pH=7.0), 1.48 g and 2.2 g of 1-CN were added (the final concentrations were 1 M and 2 M respectively), the reaction was carried out in a constant temperature water bath at 35° C. for 12 h. Samples were taken every 30 minutes, and subjected to centrifugation at 12,000 rpm for 5 minutes, then the supernatant was taken, and the concentrations of 1-CA and 1-CN in the supernatant were analyzed by HPLC. Under the same conditions, comparing with the original strain *E. coli* BL21(DE3)-AcN-M, the results were shown in FIG. 6. When catalyzing 1 M 1-CN, the reaction time required for the recombinant strain was 2 h, the reaction time of the original strain was 2.5 h, and the conversion rate of both reached more than 99%; however, in the case of 2 M substrate, after 12 h of reaction, the conversion rate of the original strain on the substrate was 77.5% due to the high substrate concentration, and the conversion rate of the recombinant strain reached 81.7% under the same conditions due to the amount increase of functional protein.

Example 7: Preparation of Gabapentin-Lactam Using 1-Cyanocyclohexyl Acetic Acid in the Conversion Solution Produced by the Whole Cell Catalyst The conversion solution from Example 6 was subjected to centrifugation (8000 rpm, 10 min) to remove the bacterial cells, and the collected filtrate was 1-cyanocyclohexyl acetic acid. 150 mL of the filtrate was placed in a hydrogenation reactor, 1.5 g of Raney nickel (RTH-4110), 1 mL of triethylamine (analytical grade) and 500 μL of formic acid (analytical grade) are added; nitrogen was pumped in to replace the air and this operation was repeated 3 times to ensure that there was no air in the reactor; then hydrogen was pumped in again (the pressure of the reaction was maintained at 2 Mpa), and the reaction was carried out at 1000 rpm for 8 hours; and after cooling, the Raney nickel was recovered by filtration, and the resulting filtrate was added with isovolumetric dichloromethane for extraction, and after standing and stratification, the organic phase was subjected to rotary evaporation at 40° C., the obtained solid was gabapentin-lactam, and the dichloromethane could be recycled for reuse. The experimental results showed that the conversion solution obtained from the whole cell catalysis can be directly used in the subsequent hydrogenation reaction, and the substrate conversion rate reached 99.6%, the yield rate of gabapentin-lactam was 95.8%, and the substrate conversion rate and the product yield met the requirements for industrially produced chemicals.

Example 8: Preparation of Pharmaceutical Chemicals-Gabapentin from Gabapentin-Lactam Obtained by Hydrogenation 76.7 g of the gabapentin-lactam obtained in Example 7 was dissolved in 500 mL of 6 M HCl solution and subjected to heating reflux for 2.5 h, after cooling to room temperature, isovolumetric dichloromethane was added extraction, after standing and stratification, the water phase was subjected to crystallization at 0-4° C. and suction filtration, the obtained white solid was ground with acetone and subjected to filtration to remove the acetone and drying at 40° C. to obtain gabapentin hydrochloride; all the obtained gabapentin hydrochloride was dissolved in 500 mL of water, heated to 40° C. and stirred at 300 rpm to be fully dissolved, after the pH was adjusted to 7.0-7.5 by 6 M NaOH, 125 mL of toluene was added and stirred at 500 rpm for 30 min; and after the stirring, the mixture was subjected to crystallization at 0-4° C. and filtration to obtain the white solid which was crude gabapentin, and the crude gabapentin was subjected to heavy crystallization with 60% methanol or isopropanol and drying to obtain gabapentin. All the unused samples and used reagents involved in the extraction, suction filtration, and filtration operations of the above experiments can be recycled. The experimental results showed that the yield of gabapentin hydrochloride reached 81%, the yield of gabapentin obtained by recrystallization reached 73.6%, and the yield of gabapentin after repeated recovery of the mother liquor for 3-5 times reached 93.2%. The yields of gabapentin and intermediates thereof have all reached a relatively high level, and multiple times of sample and reagent recovery steps reduced costs and waste water generation, which met the concept of green chemistry, and realized the high efficient production of the chemical-enzymatic method of pharmaceutical chemicals.

Example 9: Application Performance of the Polypeptide Tags on Nitrilase from Other Sources The preferred polypeptide tag GKGKG(SEQ ID NO: 3) in Example 1 was linked to N-terminal of nitrilase LNIT5 (Accession No.: AAR97494.1), nitrilase No. 385,386 (Accession No.: AY487562) and nitrilase derived from R. rhodochrous K22 (Accession No.: Q02068.1) (hereinafter referred to as RrNit) according to the method of Example 1. of nitrilase. The solubility and relative cell enzyme activity were determined according to the method of Example 3.

The results of the experiment were shown in Table 5 below, the solubility of the three different nitrilase enzymes was improved to different degrees. Among them, LNIT5 increased the most, reaching 1.9 times; and when the three nitrilase enzymes used 1-CN as the substrate, improvement level of the cell enzyme activity exceeded 150%, which fully demonstrated the universal applicability of the polypeptide tag to nitrilase from other sources.

TABLE 5

Comparison of relative enzyme activity and solubility of the nitrilase from different sources

| Nitrilase | Relative cell enzyme activity (%) | Solubility improvement factor |
| --- | --- | --- |
| LNIT5 | 190.6 | 1.9 |
| No. 385,386 | 160.5 | 1.3 |
| RrNit | 173.6 | 1.5 |

Example 10 Comparison of the Efficiency of the Original Strain and the Recombinant Strain E. coli BL21(DE3)/pET-28b(+)/GKGKG(SEQ ID NO: 3)-AcN-M in the Catalytic Synthesis of Clopidogrel Intermediate (2-Chloromandelic Acid)

5 g of the wet c of the recombinant strain E. coli BL21(DE3)/pET-28b(+)/GKGKG(SEQ ID NO: 3)-AcN-M prepared by the method in Example 3 were suspended in 100 mL of $Na_2HPO_4$—$NaH_2PO_4$ buffer (0.2 M, pH=7.0), added with o-chloromandelonitrile with the final concentrations of 1 M and 2 M respectively, and reacted in a constant temperature water bath at 35° C. for 12 h. Samples were taken every 30 minutes and subjected to centrifugation at 12,000 rpm for 5 minutes. The supernatant was taken to detect the concentrations of 2-chloromandelic acid and o-chloromandelonitrile by HPLC. Under the same conditions, with the original strain E. coli BL21(DE3)-AcN-M as a control, the results were shown in FIG. 6. When catalyzing 1 M o-chloromandelonitrile, the reaction time of the recombinant strain was 3 h, and the reaction time of the original strain was 4 h, and the conversion rate of both reached more than 99%; however, in the case of 2 M substrate, due to the high substrate concentration, after 12 h of reaction, the conversion rate of the original strain to the substrate was 60.4%, while the recombinant strain reached a conversion rate of 79.4% under the same conditions due to the increase in the amount of functional protein.

TABLE 6

Comparison of the efficiency of catalyzing the synthesis of clopidogrel intermediate by the original strain and the recombinant strain

| Nitrilase | Substrate concentration (M) | Reaction time(h) | Conversion rate(%) |
| --- | --- | --- | --- |
| E. coli BL21(DE3)/pET-28b(+)/AcN-M | 1 | 4 | 99.9 |
|  | 2 | 12 | 60.4 |
| E. coli BL21(DE3)/pET-28b(+)/GKGKG-AcN-M | 1 | 3 | 99.9 |
|  | 2 | 12 | 79.4 |

Example 11 the Application Effect of the Preferred Polypeptide Tag in Deacylase to Transform Echinocandin B to Prepare the Echinocandin B Nucleus The preferred polypeptide tag GKGKG(SEQ ID NO: 3) of Example 1 was linked to a deacylase (NC_001136.10) according to the method of Example 1, to construct the recombinant strain *E. coli* BL21(DE3)/pET-28b(+)/GKGKG (SEQ ID NO: 3)-DEA (deacylase), its solubility and enzyme activity were determined. The solubility of the deacylase with the polypeptide tag was 2.8 times higher than that of the deacylase without polypeptide tag, and its specific enzyme activity was increased by 358.5%.

The catalyst in Example 10 was replaced by 50 g/L resting cells of the recombinant *E. coli* BL21(DE3)/pET-28b(+)/GKGKG(SEQ ID NO: 3)-DEA (deacylase), and the substrate was replaced by Echinocandin B with the final concentrations of 2 g/L, the reaction time was changed to 24 h, and the others were the same as in Example 10. The substrate conversion rate reached 60.6%, while the conversion rate of the deacylase without the polypeptide tag was only 35.7%. It shows that the peptide tag has a certain degree of scalability, but how it can improve the solubility of other enzymes requires deeper discussion.

Although the present invention has been disclosed the above preferred examples, they are not intended to limit the present invention. Anyone familiar with the technology can make various changes and modifications without departing from the spirit and scope of the present invention. Therefore, the protection scope of the present invention should be defined by the claims.

The invention claimed is:

1. A recombinant nitrilase, comprising:
a polypeptide tag, wherein the polypeptide tag is attached to the recombinant nitrilase on the N terminus, wherein the polypeptide tag is selected from the group consisting of: GKGKG (SEQ ID NO: 3), GKGEG (SEQ ID NO: 4), GKGHG (SEQ ID NO: 5), GRGRG (SEQ ID NO: 6), GRGGG (SEQ ID NO: 7), GHGHG (SEQ ID NO: 8), GKGKGKG (SEQ ID NO: 26), and GKGKGKGKG (SEQ ID NO: 27), wherein the polypeptide tag is universal and enhances soluble expression of the recombinant nitrilase, wherein the recombinant nitrilase has the amino acid sequence set forth in SEQ ID NO: 1, and wherein enzyme activity of the recombinant nitrilase with the polypeptide tag is at least 101.6% of the original strain.

2. The recombinant nitrilase of claim 1, wherein the polypeptide tag is connected to the recombinant nitrilase by a linker peptide, and wherein the linker peptide is selected from the group consisting of: GKGKG-GS (SEQ ID NO: 31), GKGKG-GGS (SEQ ID NO: 32), GKGKG-GGGS (SEQ ID NO: 33), and GKGKG-GGGGS (SEQ ID NO: 34).

3. The recombinant nitrilase of claim 1, wherein the polypeptide tag is linked to a linker peptide, and the linker peptide is selected from the group consisting of: GS, GGS, GGGS (SEQ ID NO: 29), and GGGGS (SEQ ID NO: 30).

* * * * *